(12) United States Patent
Cusumano et al.

(10) Patent No.: US 11,596,781 B2
(45) Date of Patent: Mar. 7, 2023

(54) LAMPREY LOCK DEVICE

(71) Applicant: THE REGENTS OF THE UNIVERSITY OF CALIFORNIA, Oakland, CA (US)

(72) Inventors: Lucas R. Cusumano, Los Angeles, CA (US); Justin P. McWilliams, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/701,439

(22) Filed: Mar. 22, 2022

(65) Prior Publication Data
US 2022/0296872 A1 Sep. 22, 2022

Related U.S. Application Data

(60) Provisional application No. 63/164,123, filed on Mar. 22, 2021.

(51) Int. Cl.
*A61M 39/10* (2006.01)
*A61M 25/00* (2006.01)
(Continued)

(52) U.S. Cl.
CPC .... *A61M 39/1011* (2013.01); *A61M 25/0097* (2013.01); *A61M 39/12* (2013.01);
(Continued)

(58) Field of Classification Search
CPC ...... A61M 39/1011; A61M 2039/1016; A61M 39/12; A61M 2039/1033; A61M 2039/1038; A61M 39/10; A61M 2039/1083; A61M 2039/1077; A61M 2039/229; A61M 16/0833; F16L 15/003; F16L 15/008; F16L 19/00; Y10T 403/5741
See application file for complete search history.

(56) References Cited

U.S. PATENT DOCUMENTS 670,584 A * 3/1901 Fowle, Jr. ............. F16L 15/003
285/285.1
2,150,221 A * 3/1939 Hinderliter ........... F16L 15/003
285/918
(Continued)

FOREIGN PATENT DOCUMENTS

CN 112657049 A 4/2021
DE 3821154 C * 10/1989 ............ A61M 39/10
(Continued)

OTHER PUBLICATIONS

Translation of Tsubooka et al. (WO 2015146310 A1) (Year: 2015).*
(Continued)

*Primary Examiner* — Nilay J Shah
(74) *Attorney, Agent, or Firm* — Riverside Law, LLP

(57) ABSTRACT

The present invention provides a lamprey lock device configured to provide a fluid transfer between two devices or objects. In one embodiment, lamprey lock device of the present invention improves fluid transfer by maximizing the inner diameter of connections between two objects including but not limited to a catheter, tubing, veress needles, trocars, syringes, or gas/fluid delivery systems.

19 Claims, 38 Drawing Sheets

(51) Int. Cl.
*A61M 39/22* (2006.01)
*A61M 39/12* (2006.01)
A61M 39/06 (2006.01)
A61M 39/26 (2006.01)

(52) U.S. Cl.
CPC ....... *A61M 39/22* (2013.01); *A61M 2039/062* (2013.01); *A61M 2039/1016* (2013.01); *A61M 2039/1077* (2013.01); *A61M 2039/229* (2013.01); *A61M 2039/262* (2013.01)

(56) References Cited

U.S. PATENT DOCUMENTS

| | | | | |
|---|---|---|---|---|
| 2,246,436 | A * | 6/1941 | Downey | F16L 15/00 285/349 |
| 2,562,294 | A * | 7/1951 | Cahenzli, Jr. | F16L 19/0218 285/356 |
| 2,711,913 | A * | 6/1955 | Jungblut | F16L 27/1017 285/379 |
| 2,825,584 | A * | 3/1958 | Badger | F16L 15/008 285/286.1 |
| 3,472,533 | A * | 10/1969 | Turner | F16L 15/04 285/55 |
| 4,676,530 | A * | 6/1987 | Nordgren | A61M 39/1011 411/521 |
| 5,300,046 | A | 4/1994 | Scarfone | |
| 5,400,995 | A * | 3/1995 | Boyd | A61M 5/1415 248/407 |
| 5,533,983 | A * | 7/1996 | Haining | A61M 39/04 604/249 |
| 6,248,092 | B1 * | 6/2001 | Miraki | A61M 25/00 604/905 |
| 7,857,805 | B2 | 12/2010 | Raines | |
| 8,388,603 | B1 * | 3/2013 | Friedman | A61M 39/22 604/537 |
| 8,613,738 | B2 | 12/2013 | Mantell | |
| 9,468,749 | B2 | 10/2016 | Mansour | |
| 9,920,866 | B2 | 3/2018 | Crompton | |
| 2002/0101079 | A1 | 8/2002 | Ehrke | |
| 2003/0006610 | A1 * | 1/2003 | Werth | B25B 27/10 285/322 |
| 2003/0193190 | A1 * | 10/2003 | Werth | F16L 33/225 285/243 |
| 2005/0192559 | A1 * | 9/2005 | Michels | A61M 39/1011 604/533 |
| 2008/0004600 | A1 | 1/2008 | Kitani | |
| 2010/0049144 | A1 | 2/2010 | Mcconnell | |
| 2012/0200081 | A1 | 8/2012 | Reznar | |
| 2013/0041313 | A1 * | 2/2013 | Chung | A61M 1/84 604/31 |
| 2013/0131608 | A1 * | 5/2013 | Davis | A61M 39/287 604/250 |
| 2014/0265319 | A1 | 9/2014 | Clark | |
| 2016/0067148 | A1 * | 3/2016 | Nordquist | A61M 5/1415 604/28 |
| 2016/0305574 | A1 * | 10/2016 | Burdge | A61M 39/26 |
| 2017/0014615 | A1 * | 1/2017 | Hofstetter | A61F 13/00068 |
| 2018/0245721 | A1 * | 8/2018 | Braathen | F16L 19/0286 |
| 2019/0151642 | A1 * | 5/2019 | Becker | A61M 39/10 |

FOREIGN PATENT DOCUMENTS

| | | | | |
|---|---|---|---|---|
| WO | WO-2008086631 | A1 * | 7/2008 | ............ A61M 1/285 |
| WO | 2013056273 | A2 | 4/2013 | |
| WO | WO-2015146310 | A1 * | 10/2015 | ........ A61M 25/0097 |
| WO | 2020146454 | A1 | 7/2020 | |

OTHER PUBLICATIONS

Eloot S, De Vos J-Y, Hombrouckx R, Verdonck P. How much is catheter flow influenced by the use of closed luer lock access devices? Nephrology Dialysis Transplantation. 2007;22(10):3061-4.

Park JK, Kraus FC, Haaga JR. Fluid flow during percutaneous drainage procedures: an in vitro study of the effects of fluid viscosity, catheter size, and adjunctive urokinase. American Journal of Roentgenology 1993;160(1):165-9.

* cited by examiner

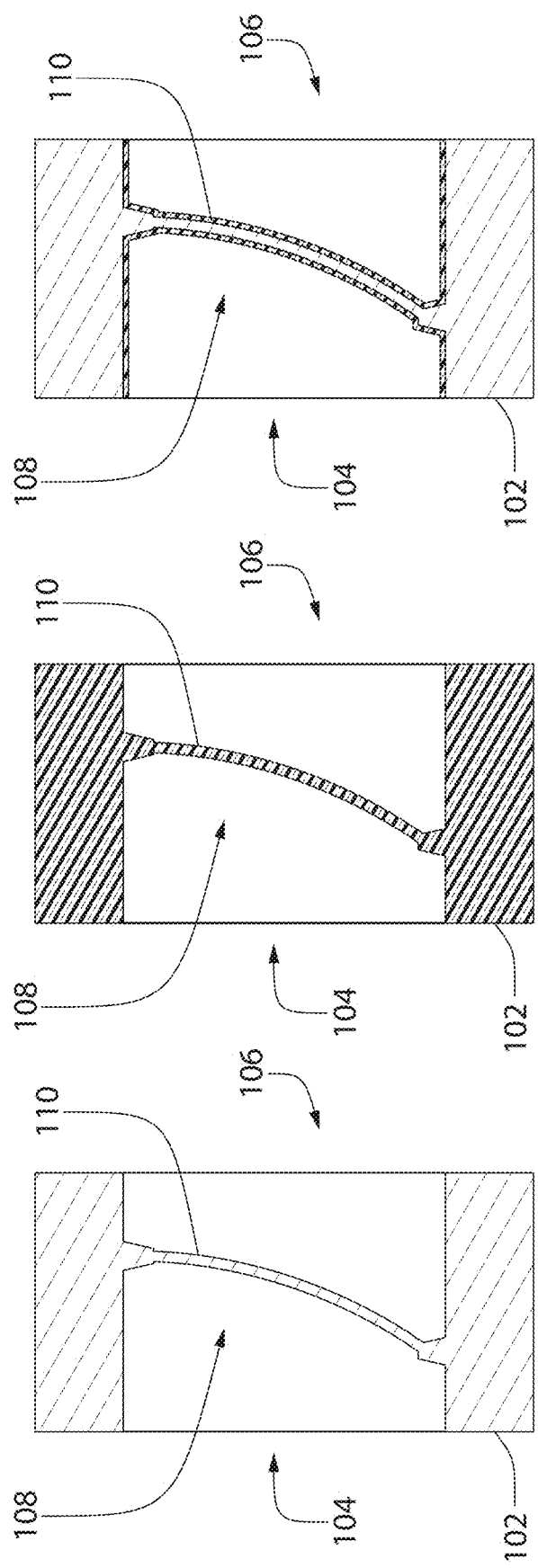

|  | Luer connector (95% CI) | Lamprey lock (95% CI) |
|---|---|---|
| Mean drainage time (sec) | 149.4 (146.7-152.1) | 112.2 (109.5-114.9) |
| Mean drainage rate (cc/sec) | 3.336 (3.275-3.457) | 4.427 (4.276-4.578) |

LAMPREY LOCK DEVICE

CROSS-REFERENCE TO RELATED APPLICATIONS

This application claims priority to U.S. Provisional Patent Application No. 63/164,123 filed Mar. 22, 2021, the contents of which are incorporated by reference herein in its entirety.

BACKGROUND OF THE INVENTION

Connections between catheters/tubing are necessary for a wide range of medical procedures including but not limited to drainage of intracorporal fluid collections, intravenous access and etc. to form a secure, leak-free connection for the transfer of fluids or gasses between the two devices or objects.

Larger diameter catheters have the advantage of more rapid flow of fluids. However, flow rates can be limited at connections due to the smaller diameter of the connection compared to the remainder of the catheter.

Thus, there is a need in the art for a connector device that allows connection of catheters/tubing with a larger inner diameter when compared to the widely utilized luer lock connection to minimize flow disturbance. The present invention meets this need.

SUMMARY OF THE INVENTION

In one aspect, the present invention provides a lamprey lock device comprising: a tubular shaped housing having a proximal end, a distal end and length therebetween, the housing further having an external surface and an internal surface, such that a lumen is formed within the internal surface along its length; an O-ring positioned within the lumen at the distal end; a first luer taper adapter positioned within the lumen and proximal to the O-ring, wherein the first luer taper adapter has a threaded internal surface; and an elastomeric ring positioned within the lumen and proximal to the first luer taper adapter. In one embodiment, the O-ring, the first luer taper adapter and the elastomeric ring each has an internal diameter equal to or greater than 4 mm. In one embodiment, the lamprey lock device further comprising a second luer taper adapter positioned within the lumen and proximal to the elastomeric ring, wherein the second luer taper adapter has a threaded internal surface. In one embodiment, the elastomeric ring has a width of greater than 1 mm. In one embodiment, the lamprey lock device further comprising an elastomeric coating on the internal surface of the first luer taper adapter. In one embodiment, the threaded internal surface of the first luer taper adapter has a spiral rotation of at least 0.5. In one embodiment, the elastomeric ring has an interior diameter ranging between 5-8 mm. In one embodiment, the device further comprises a three-way stopcock comprising: a tubular body having a first tube section, a second tube section and a third tube section, wherein each of the first, second and third tube sections comprises a lumen and are fluidly connected at a first end to a central connector and terminate in an opening at a second end opposite to the first end; and a central component comprising a circumference that is slightly less than a circumference of the central connector, such that central component may be inserted within the central connector with minimal tolerance, and wherein the central component comprises a first open side, a second open side, a third open side, and a closed side; wherein the second end of the first tube section is connected to the distal end of the lamprey lock device; wherein the second end of the second tube section is fluidly connected to a flush pump; and wherein the second end of the third tube section is fluidly connected to a drainage reservoir. In one embodiment, the stopcock comprises: a drain mode, wherein the central component produces a patent channel from the first open side and the third open side into a drainage reservoir; and a flush mode, wherein the central component produces a patent channel from a flush reservoir through the first open side and the second open side into a catheter connected to the lamprey lock device. In one embodiment, the device further comprises a tubing having a proximal end, a distal end, and a body therebetween connected to the distal end of the housing, wherein the body comprises a first opening at the proximal end and a second opening at the distal end, a third opening therebetween and a side port, wherein the side port is fluidly connected to the body through the third opening. In one embodiment, the side port comprises a first end, a second end and a lumen therebetween, wherein the second end comprises an opening, sized and configured to connect to standard sizing for luer connectors. In one embodiment, the side port further comprises a valve member configured to allow selective fluid communication between the body and the side port, wherein the valve member comprises a compressible component configured to receive the luer tip of a syringe at the second end, a support structure configured to guide the compressible component through its travel along the lumen from the second end to the first end and at least one channel configured to open when the compressible component receives the luer tip of a syringe. In one embodiment, the device further comprises a flow switch positioned on the body and distal to the side port. In one embodiment, the flow switch comprises a tab, a track configured to allow longitudinal movement of the tab between an open and close position, a compressible tubing positioned, and an occluding member configured to move vertically pushing on the compressible tubing causing flow restriction between the body and a drainage reservoir. In one embodiment, the device further comprises an external clamp positioned distal to the side port and around the body. In one embodiment, the external clamp comprises a rounded opening and an occluded slot, wherein the rounded opening converges to create a narrow width of the occluded slot, and wherein when body is forced into the occluding slot, the side wall of the body is pinched together and prevents the flow of fluid therethrough. In one embodiment, the device further comprises a chamber positioned anywhere between the first opening and the second opening and is configured to engage the exterior surface of the body. In one embodiment, the chamber further comprises a first end, a second end, and a side port positioned at the first end and a bottom part positioned at the second end, and wherein the side port is fluidly connected to the body through a side channel. In one embodiment, the side port comprises a valve member configured to allow selective fluid communication between the body and the side port, wherein the valve member comprises a compressible component configured to receive the luer tip of syringe and a tip positioned below the compressible component, wherein once the syringe is inserted, the luer tip pushes the compressible component down on the body all the way to the bottom part, which in turn causes the side channel to open and allow fluid communication between the side port and the body. In one embodiment, the tip is a pointed tapered tip of at least 45 degrees.

In one aspect, the present invention provides a method of draining a body cavity comprising the steps of: providing a lamprey lock device comprising a tubular shaped housing having a proximal end, a distal end and length therebetween, the housing further having an external surface and an internal surface, such that a lumen is formed within the internal surface along its length; an O-ring positioned within the lumen at the distal end; a first luer taper adapter positioned within the lumen and proximal to the O-ring, wherein the first luer taper adapter has a threaded internal surface; and an elastomeric ring positioned within the lumen and proximal to the first luer taper adapter; inserting a catheter into the proximal end of the lamprey lock device, engaging the plurality of threads with clockwise rotation; placing a tubing at the distal end of the lamprey lock device comprising a proximal end, a distal end and a body therebetween; passing through a liquid through the catheter and the tubing.

BRIEF DESCRIPTION OF THE DRAWINGS

The following detailed description of invention will be better understood when read in conjunction with the appended drawings. It should be understood, however, that the invention is not limited to the precise arrangements and instrumentalities of the embodiments shown in the drawings.

FIG. 2 depicts a sagittal cross section of an exemplary lamprey lock device of the present invention wherein the lamprey lock device is made of a rigid plastic material.

FIG. 3 depicts a sagittal cross section of an exemplary lamprey lock device of the present invention wherein the inner surface of the lumen of the lamprey lock device is covered with an elastomeric material.

FIG. 4 depicts a sagittal cross section of an exemplary lamprey lock device of the present invention wherein the lamprey lock device is made of a rigid plastic core and an elastomeric material covering the inner surface of the lumen.

DETAILED DESCRIPTION

Figure 1:
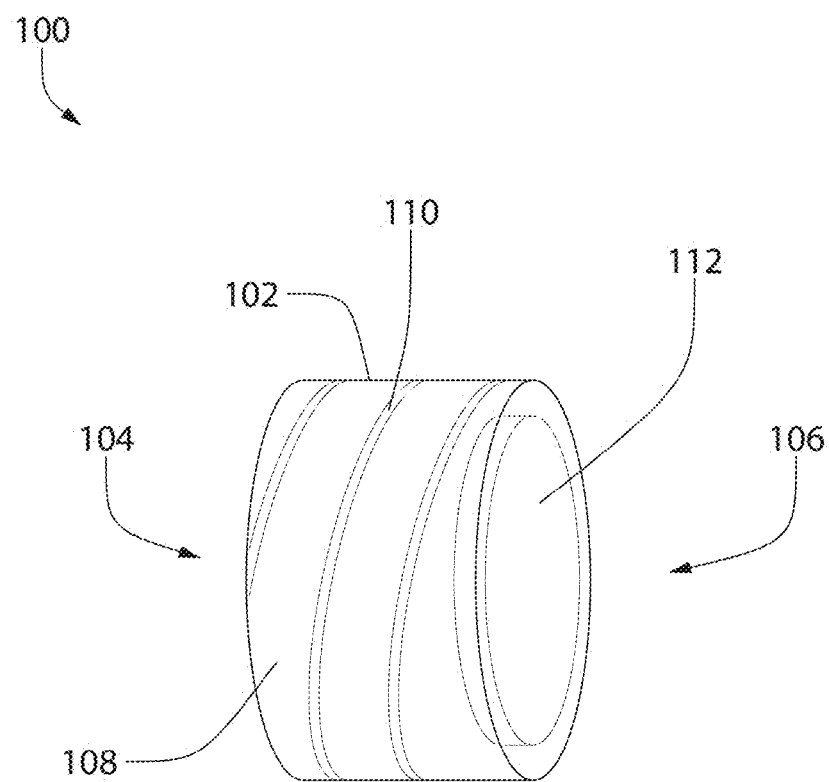
FIG. 1 depicts a side view of an exemplary lamprey lock device of the present invention.

It is to be understood that the figures and descriptions of the present invention have been simplified to illustrate elements that are relevant for a clear understanding of the present invention, while eliminating, for the purpose of clarity many other elements found in the field of adaptors. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Definitions

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Lamprey Lock

The present invention provides a lamprey lock device configured to provide a fluid transfer between two devices or objects. In one embodiment, lamprey lock device of the present invention improves fluid transfer by maximizing the inner diameter of connections between two objects including but not limited to a catheter, tubing, veress needles, trocars, syringes, or gas/fluid delivery systems. In one embodiment, lamprey device of the present invention is fully compatible with two objects utilizing a female luer lock distal end. In one embodiment, the lamprey device of the present invention provides a connection between a catheter at its proximal end to tubing including but not limited to a drainage reservoir tubing. In one embodiment, the lamprey device of the present invention allows health care institutions to continue using current catheter designs with the added benefit of increasing minimal inner diameter at connections with the lamprey lock device. In one embodiment, while maintaining compatibility, cross-sectional area of connections with the lamprey lock device can be maximized to 13 mm$^2$ compared to 3 mm$^2$ with traditional luer lock connections.

Referring now to FIG. 1, an exemplary lamprey lock device 100 of the present invention is shown. Lamprey lock device 100 comprises a luer taper adapter 102 having a proximal end 104, a distal end 106 and forming a lumen 108 therebetween. The inner surface forming lumen 108 may be smooth, barbed, tapered, threaded, or have any other surface topography to assist securing a conduit to it. In one embodiment, the inner surface of lumen 108 may comprise a plurality of threads 110 on all or a portion of the interior wall within lumen 108 of luer taper adapter 102. In one embodiment, plurality of threads 110 may be a left-handed helical thread. In one embodiment, plurality of threads 110 may be a right-handed helical thread. As contemplated herein, lumen 108 may have an internal, cross-sectional diameter between 1-8 mm. In some embodiments, lumen 108 may have a cross-sectional diameter between 6-8 mm. In some embodiments, the cross sectional diameter of lumen 108 is equal or greater than 1 mm, equal or greater than 2 mm, equal or greater than 3 mm, equal or greater than 4 mm, equal or greater than 5 mm, equal or greater than 6 mm, equal or greater than 7 mm, or equal or greater than 8 mm. In one embodiment, lumen 108 and plurality of threads 110 may be sized to comply with the widely used 6% luer taper used for intravascular and hypodermic applications (international Organization of Standard ("ISO") standards 80369-7). In one embodiment, lumen 108 may comprise any number of thread configurations available to provide and interlock between medical devices. In one embodiment, plurality of threads 110 have a spiral rotation of at least 0.5. It should be appreciated that there is no limitation to the size, profile, and pitch of threads 110 of luer taper 102.

In one embodiment, lumen 108 may have a length ranging between 1-12 mm. In some embodiments, lumen 108 may have a length between 8 mm and 10 mm. In some embodiments, the length of 108 is equal or greater than 1 mm, equal or greater than 2 mm, equal or greater than 3 mm, equal or greater than 4 mm, equal or greater than 5 mm, equal or greater than 6 mm, equal or greater than 7 mm, equal or greater than 8 mm, equal or greater than 9 mm, or equal or greater than 10 mm.

Luer taper adapter 102 may further include an O-ring 112, positioned within lumen 108, configured to create a water-tight seal with the proximal end of the inserted object including but not limited to a catheter. In one embodiment, O-ring 112 may be positioned at or near distal end 106 of lumen 108. In one embodiment, O-ring 112 may comprise rubber, silicone, PVC, or any other material operative to provide a seal to the surface of the mating connector to prevent fluids or gasses from leaking around O-ring 112 or passing through O-ring 112 itself. In one embodiment, O-ring 112 may have a maximum outer diameter of 8 mm. In one embodiment, O-ring 112 may have a maximum inner diameter of 4 mm.

Luer taper adapter 102 may be made from any suitable material including but not limited to metal, plastic, an elastomeric material, or combinations thereof (FIG. 2, FIG. 3, and FIG. 4). In one embodiment, luer taper adapter 102 may be made from a rigid material. In one embodiment, luer taper adapter 102 may be made from an elastomeric material. In one embodiment, the inner surface of luer taper adapter 102 may be covered with a covering or coating 107. In one embodiment, coating or covering 107 may be elastomeric. In one embodiment, covering or coating 107 may be a rigid plastic. Covering or coating 107 is configured to cover the inner surface of luer taper adapter 102 within lumen 108 to create a watertight seal. In one embodiment, plastic materials for any components of device 100 may include but are not limited to polycarbonate, polyethylene, polypropylene, polyesters, and co-polyesters. In one embodiment, elastomeric material for any components of device 100 may include but are not limited to silicone, silicone rubber, or polyisoprene.

Figure 5:
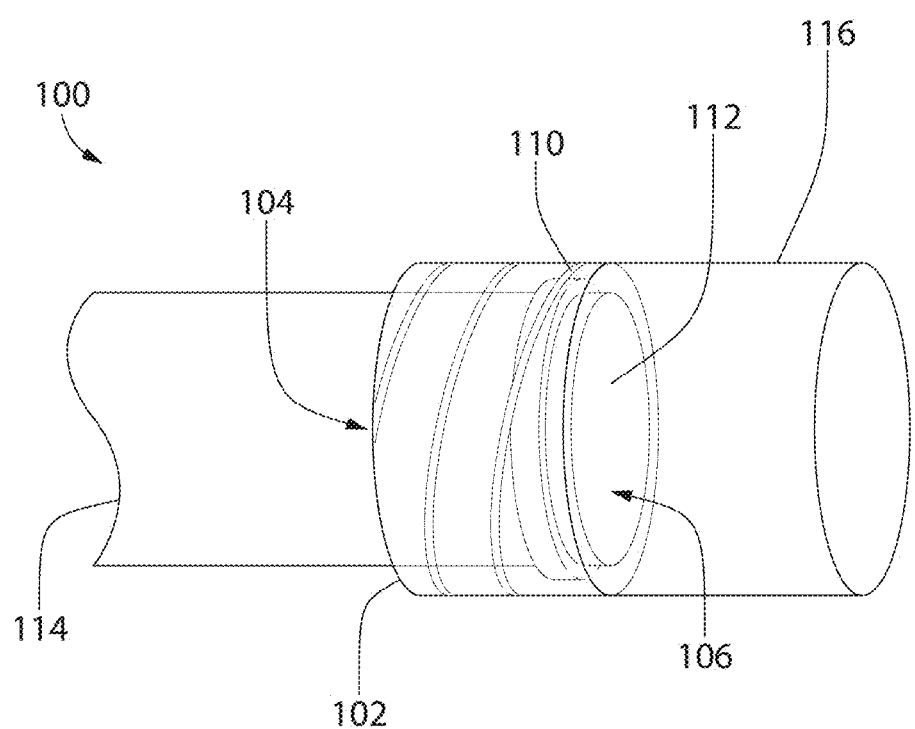
FIG. 5 depicts a side view of a catheter connection with the lamprey lock device.
Figure 6:
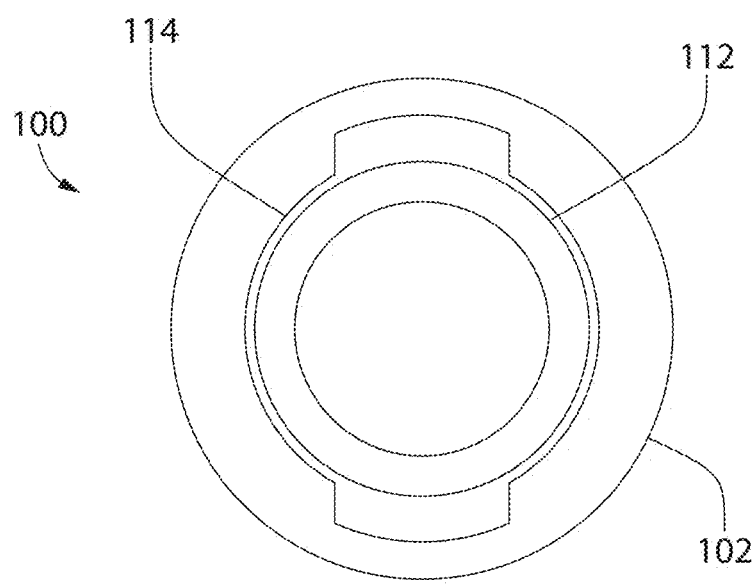
FIG. 6 depicts a coronal view of a catheter connection with the lamprey lock device.

Referring now to FIG. 5 and FIG. 6, an exemplary catheter 114 connection with luer taper adapter 102 is shown. In one embodiment, a catheter 114 may be inserted into lumen 108 at proximal end 104, engaging plurality of threads 110 with clockwise rotation to create a watertight seal with O-ring 112 at distal end 106. Catheter 114 may be disconnected from luer taper adapter 102 with a counter-clockwise rotation. In other embodiments, any other medical device may be inserted at proximal end 104 with clockwise rotation. In one embodiment, catheter 114 may be any catheter including but not limited to drainage catheter, vascular access, urinary and biliary catheter. It should be appreciated that any similarly tube-shaped and/or tapered device that permits flow therethrough (flexible, rigid expandable and/or extendable) may be suitable for insertion into proximal end 104. In one exemplary embodiment, a tubing 116 may be inserted at distal end 106. Tubing 116 may be attached to the outer surface of lumen 108 at distal end 106.

Figure 7:
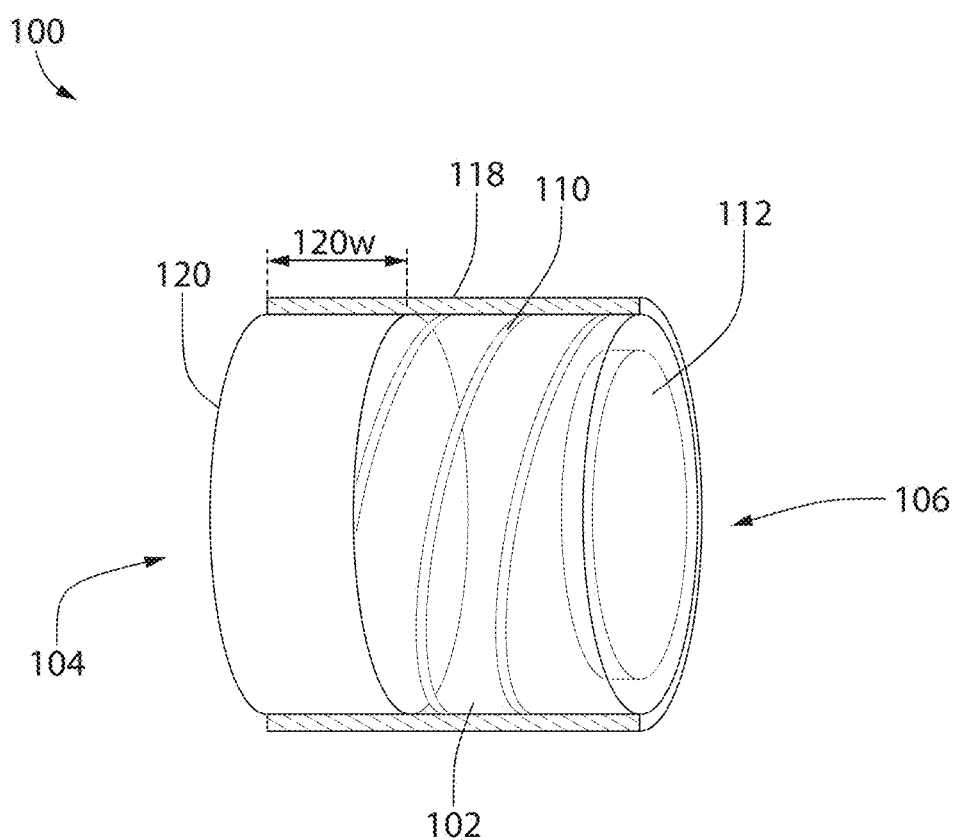
FIG. 7 depicts a side view of an exemplary lamprey lock device of the present invention comprising a circumferential elastomeric seal.

In one embodiment, lamprey lock device 100 may further comprise a covering or housing 118 (FIG. 7), configured to secure components of device 100 together. In some embodiments, covering or housing 118 may be generally tubular or cylindrical in shape. However, it should be appreciated that there are no limitations to the shape of covering 118, such that the internal components of device 100 can be positioned securely therein. In one embodiment, covering 118 may be made from materials including but not limited to metal, plastic, an elastomeric material, or combinations thereof.

In one embodiment, lamprey lock device 100 may further comprise a circumferential elastomeric seal 120 positioned at or near proximal end 104, configured to create an additional watertight seal around the inserted medical device including but not limited to a catheter. In one embodiment, circumferential elastomeric seal 120 is configured to create an additional watertight seal in the event the user has not fully tightened the medical device within the luer taper adapter portion 102. In one embodiment, elastomeric seal 120 may be made from materials including but not limited to rubber, silicone and etc. In one embodiment, the elastomeric seal may be composed of an open cell matrix made from material including but not limited to polyurethane, polyethylene and etc. In one embodiment, circumferential elastomeric seal 120 has an inner diameter ranging between 4-8 mm. In some embodiments, the circumferential elastomeric seal 120 has an inner diameter ranging from 5-7 mm. In some embodiments, circumferential elastomeric seal 120 inner diameter is equal or greater than 4 mm, equal or greater than 5 mm, equal or greater than 6 mm, equal or greater than 7 mm, or equal or greater than 8 mm.

In one embodiment, circumferential elastomeric seal 120 has a thickness ranging between 1-6 mm. In some embodiments, the circumferential elastomeric seal 120 has a thickness ranging from 2-4 mm. In some embodiments, circumferential elastomeric seal 120 has a thickness equal or greater than 1 mm, equal or greater than 2 mm, equal or greater than 3 mm, equal or greater than 4 mm, equal or greater than 5 mm, or equal or greater than 6 mm.

In one embodiment, circumferential elastomeric seal 120 has a width 120w ranging between 1-6 mm. In some embodiments, the circumferential elastomeric seal 120 has a width ranging from 1-3 mm. In some embodiments, circumferential elastomeric seal 120 has a width equal or greater than 1 mm, equal or greater than 2 mm, equal or greater than 3 mm, equal or greater than 4 mm, equal or greater than 5 mm, or equal or greater than 6 mm.

In one embodiment, covering 118 is positioned around luer taper adapter 102 and circumferential elastomeric seal 120 to secure them together.

Figure 8:
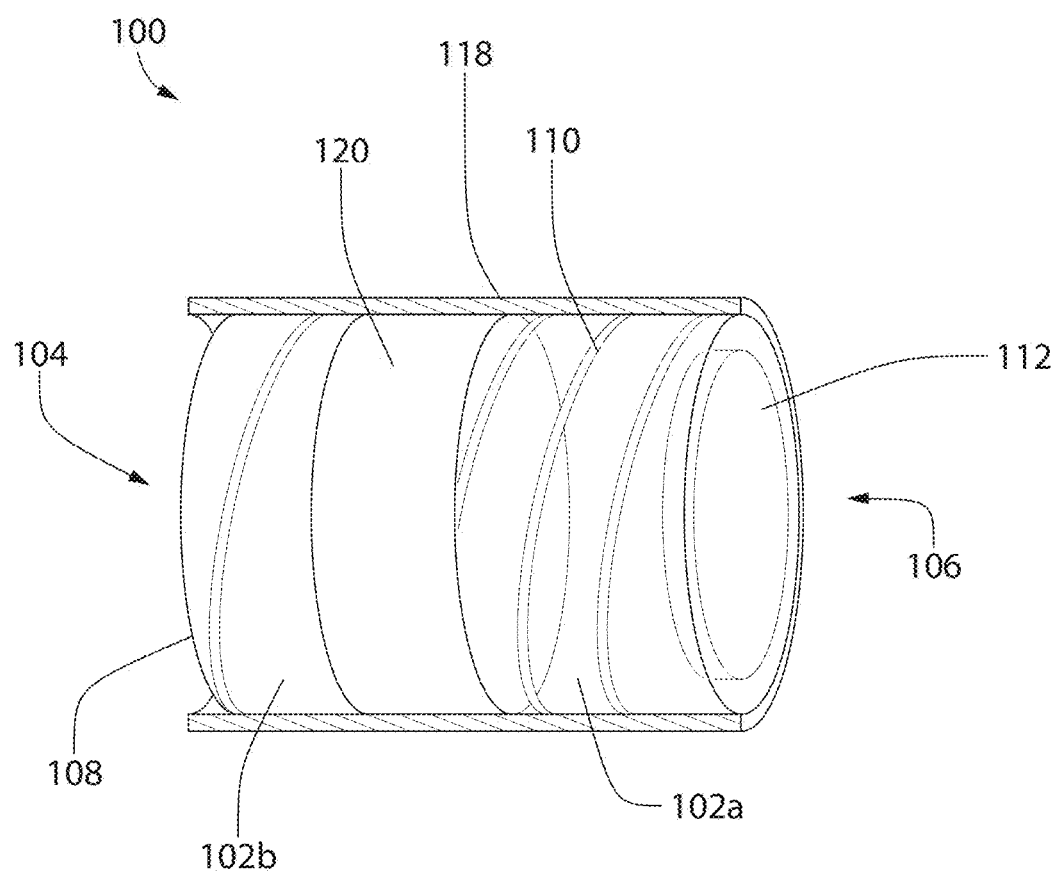
FIG. 8 depicts a side view of an exemplary lamprey lock device of the present invention comprising a second luer taper positioned proximal to the circumferential elastomeric seal.
Figure 9:
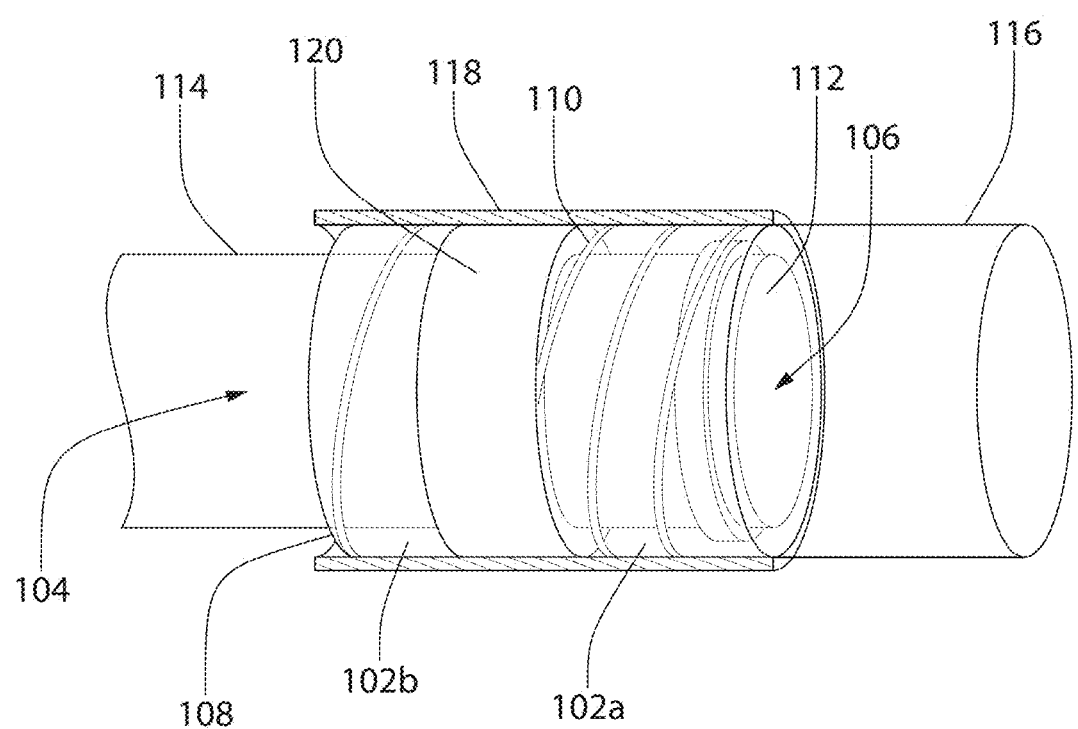
FIG. 9 depicts a side view of an exemplary lamprey lock device of the present invention connected to a drainage catheter.

Referring now to FIG. 8, in one embodiment, a second luer taper adapter 102b may be positioned proximal to circumferential elastomeric seal 120, and held together with covering 118. In one embodiment, rotational motion allows for catheter 114 to pass through circumferential elastomeric seal 120 more easily. In one embodiment, when catheter 114 is advanced through the luer taper adapters 102a and 102b and circumferential elastomeric seal 120, watertight seals are created at the side of catheter 114 and at distal end 106 to prevent the leakage of fluid (FIG. 9). It should be appreciated that device 100 may include one or a plurality of luer taper adapters, and zero, one or a plurality of elastomeric seals. It should further be appreciated that the configuration of luer taper portions and elastomeric seal portions can be in any combination. For example, device 100 may include one or more luer tapers, and/or one or more elastomeric seals. For example, In one embodiment, device 100 may include, from proximal end to distal end, a single luer taper adapter and an O-ring. In another embodiment, device 100 may include, from proximal end to distal end, an elastomeric seal, a luer taper adapter and an O-ring. In another embodiment, device 100 may include, from proximal end to distal end, a first luer taper adapter, elastomeric seal, a second luer taper adapter, and an O-ring. In another embodiment, device 100 may include, from proximal end to distal end, a first luer taper adapter, a second luer taper adapter, and an O-ring, where the first and second luer taper adapters have a space between them. In another embodiment, device 100 may include, from proximal end to distal end, an elastomeric seal, a first luer taper adapter, a second luer taper adapter, and an O-ring, where the first and second luer taper adapters have a space between them. It should further be appreciated that the O-ring, luer taper adapters and elastomeric seals when adjacent to each other may be in direct contact or spaced apart, in any combination.

Figure 10:
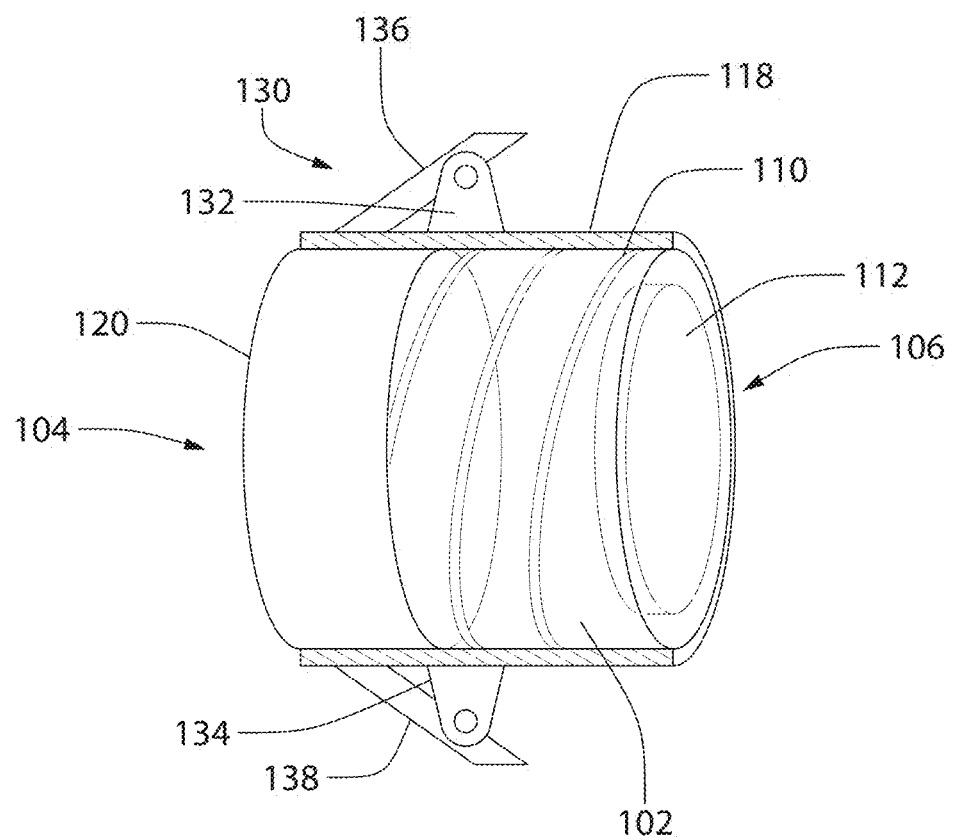
FIG. 10 depicts a side view of an exemplary lamprey lock device of the present invention comprising an external clamp in a closed position.
Figure 11:
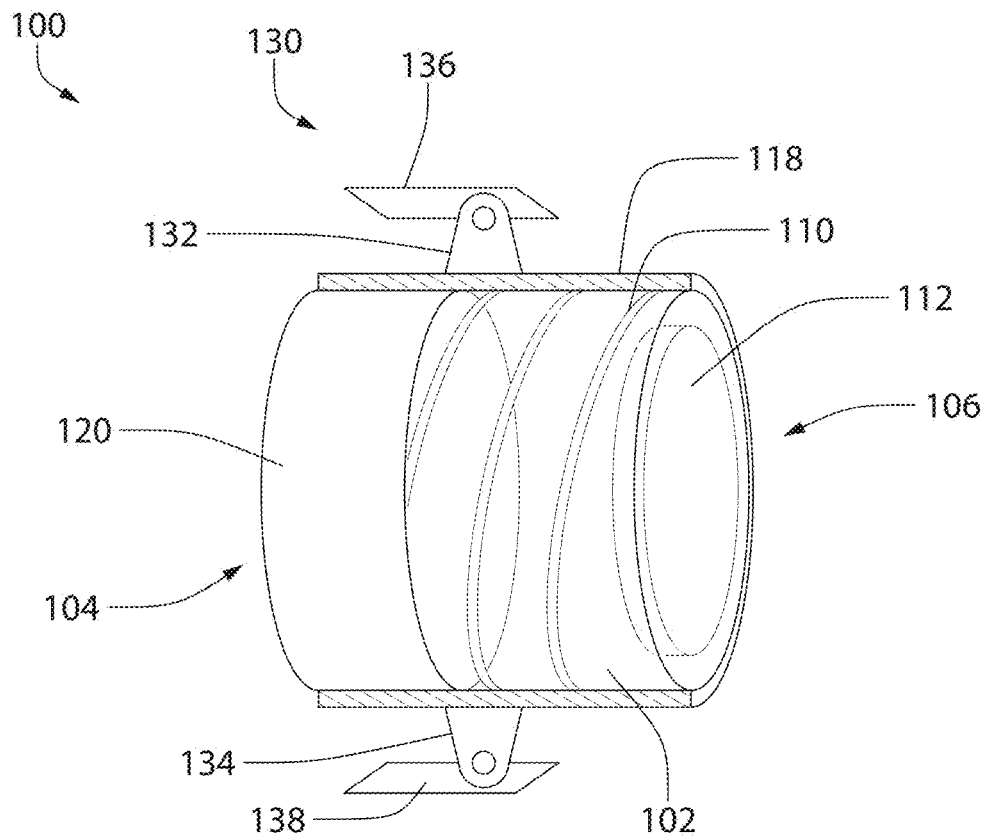
FIG. 11 depicts a side view of an exemplary lamprey lock device of the present invention comprising an external clamp in an open position.

In one embodiment, lamprey lock device 100 may further comprise an external clamp 130 positioned around covering 118 on top of elastomeric seal 120, configured to allow insertion and withdrawal of catheter 114 or any other medical device from device 100. In one embodiment, external clamp 130 may be fastened around elastomeric seal 120 by any methods known to one skilled in the art. In one embodiment, external clamp 130 comprises a first attachment point 132, a second attachment point 134, a first articulating arm 136 having a proximal end 135, a distal end 137 and a length therebetween, and a second articulating arm 138 having a proximal end 139, a distal end 141 and a length therebetween. First attachment point 132 and second attachment point 134 are attached to the outer surface of covering 118 and are hingedly connected to first articulating arm 136 and second articulating arm 138. In one embodiment, first attachment point 132 and second attachment point 134 may be connected to first articulating arm 136 and second articulating arm 138 at any point on their length, such that pushing one end of articulating arms 136 and 138, causes the other end to move in the opposite direction and thereby release from pushing circumferential elastomeric seal 120 down and create a seal (FIG. 10 and FIG. 11).

Figure 12:
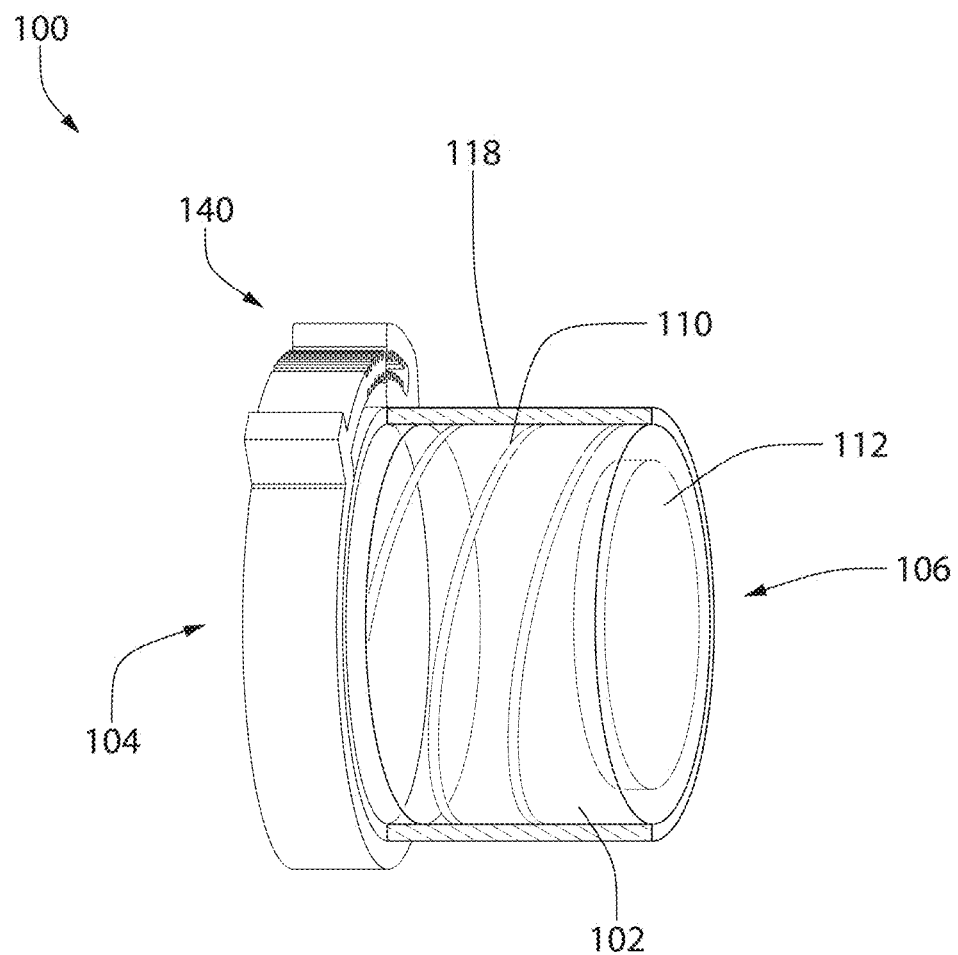
FIG. 12 depicts a side view of an exemplary lamprey lock device of the present invention comprising an external clamp in a closed position.
Figure 13:
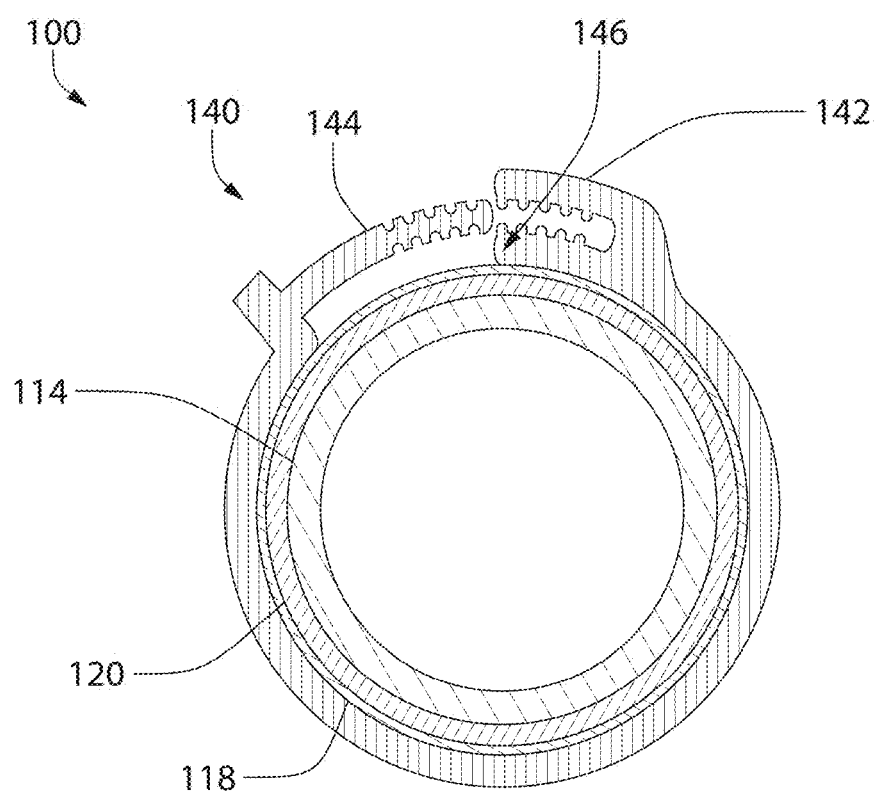
FIG. 13 depicts a coronal view of an exemplary lamprey lock device of the present invention comprising an external clamp in an open position.
Figure 14:
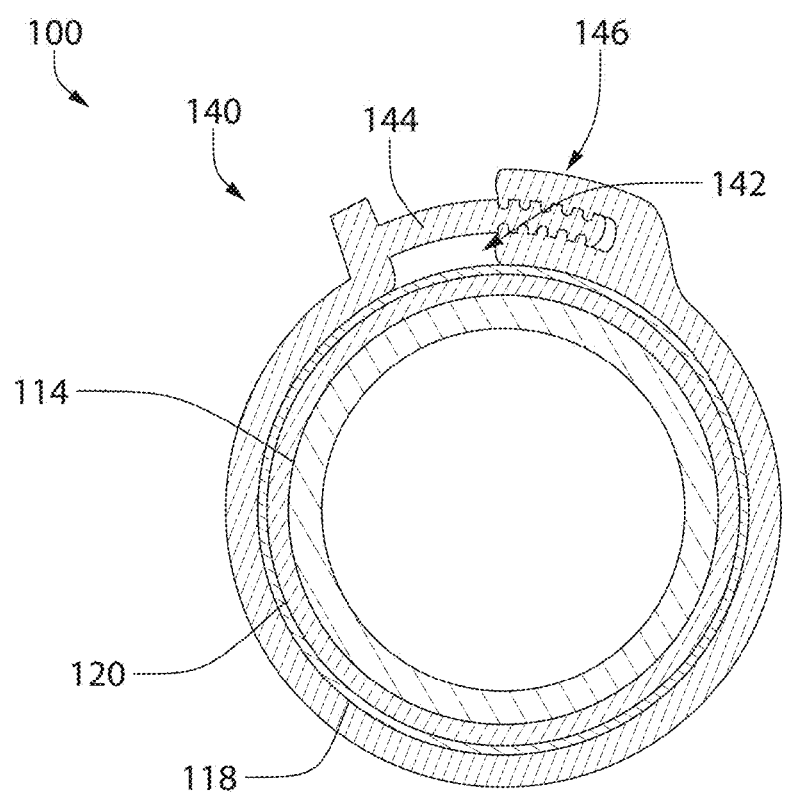
FIG. 14 depicts a coronal view of an exemplary lamprey lock device of the present invention comprising an external clamp in a closed position.

Referring now to FIG. 12 through FIG. 14, another exemplary external clamp 140 is shown. External clamp 140 may comprise an opening 142 for inserting circumferential elastomeric seal 120 therein, a first end 144 and a second end 146. First end 144 and second end 146 may comprise one or more tightening elements to allow fasten and tighten the clamp by applying a radially inward clamping force on the circumferential elastomeric seal 120 inserted in opening 142. In one embodiment, first end 144 and second end 146 may be interlocking arms.

In one embodiment, first end 144 may comprise a single ridge arm and second end 146 may comprise a double ridge arm structure, such that the single ridge can be secured and fastened between the double ridge and lead to locking of clamp 140 around circumferential elastomeric seal 120.

Figure 15:
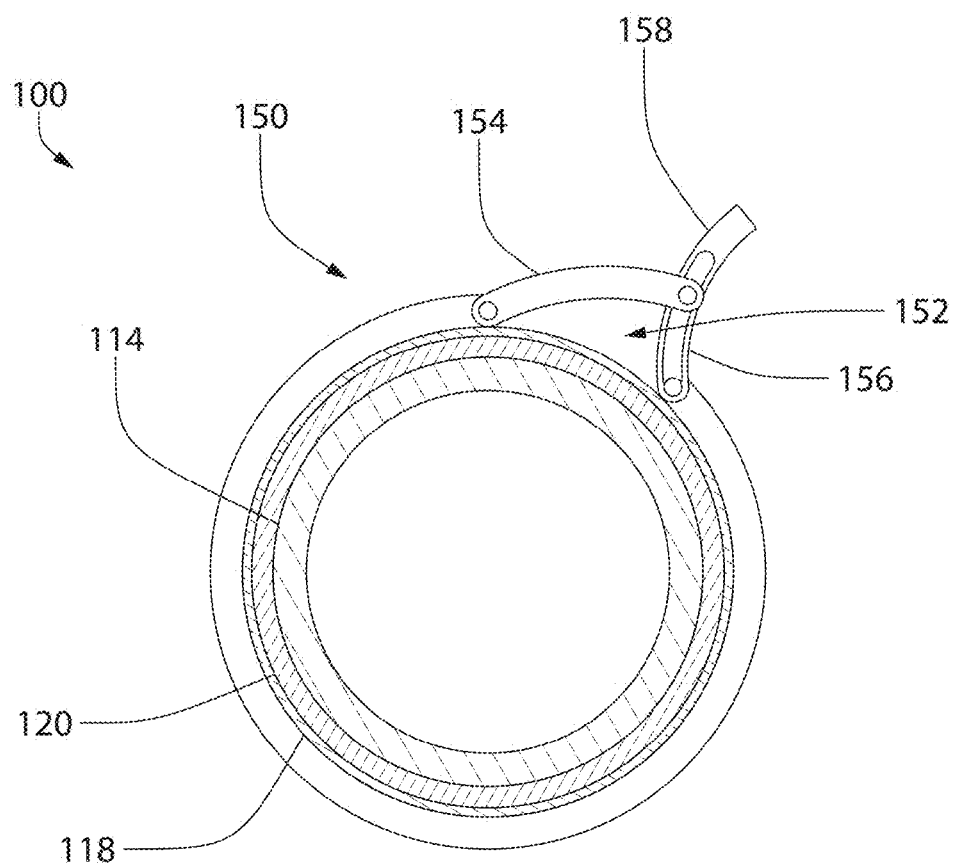
FIG. 15 depicts a coronal view of an exemplary lamprey lock device of the present invention comprising an external lever-clamp in an open position.
Figure 16:
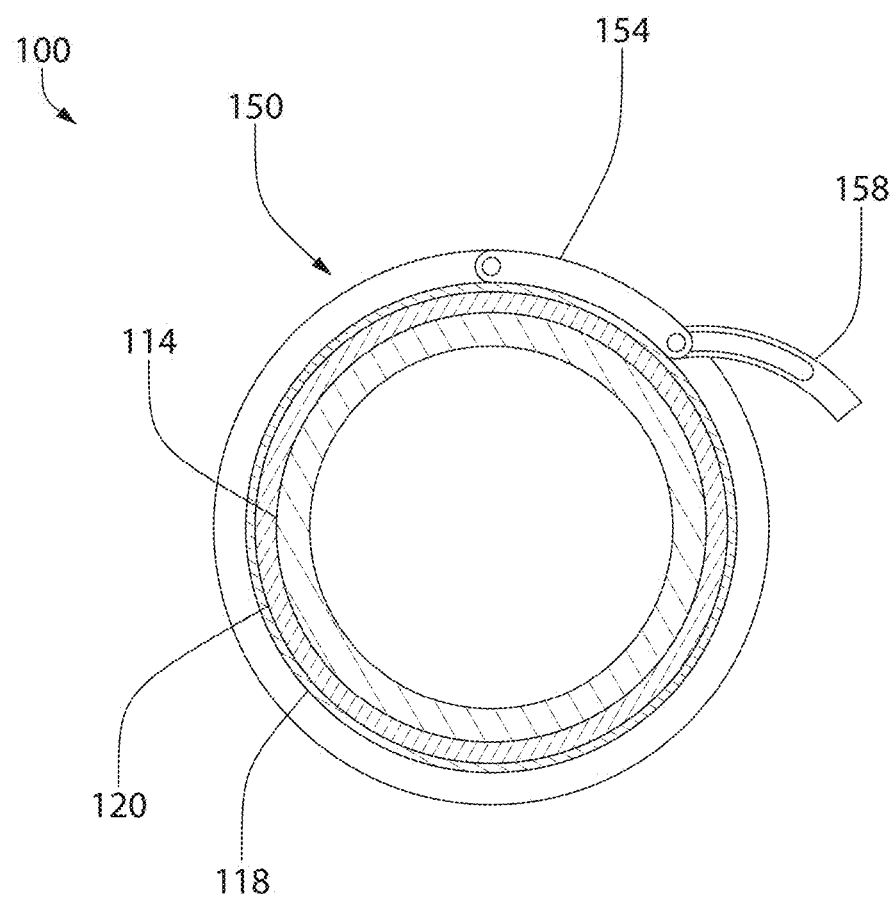
FIG. 16 depicts a coronal view of an exemplary lamprey lock device of the present invention comprising an external lever-clamp in a closed position.

Referring now to FIG. 15 and FIG. 16, another exemplary external clamp 150 is shown. External clamp 150 may be a lever-type clamp. External clamp 150 may comprise an opening 152 for inserting circumferential elastomeric seal 120 therein, a first end 154 and a second end 156. First end 154 and second end 156 may be hingedly connected to each other and a lever 158, such that upon manipulation of the lever in one direction first end 154 and second end 156 can be drawn tight around circumferential elastomeric seal 120.

In one embodiment, external clamp 130 may be made with any suitable material known to one skilled in the art including but not limited to a flexible metal sheet, a flexible plastic, etc.

Figure 17:
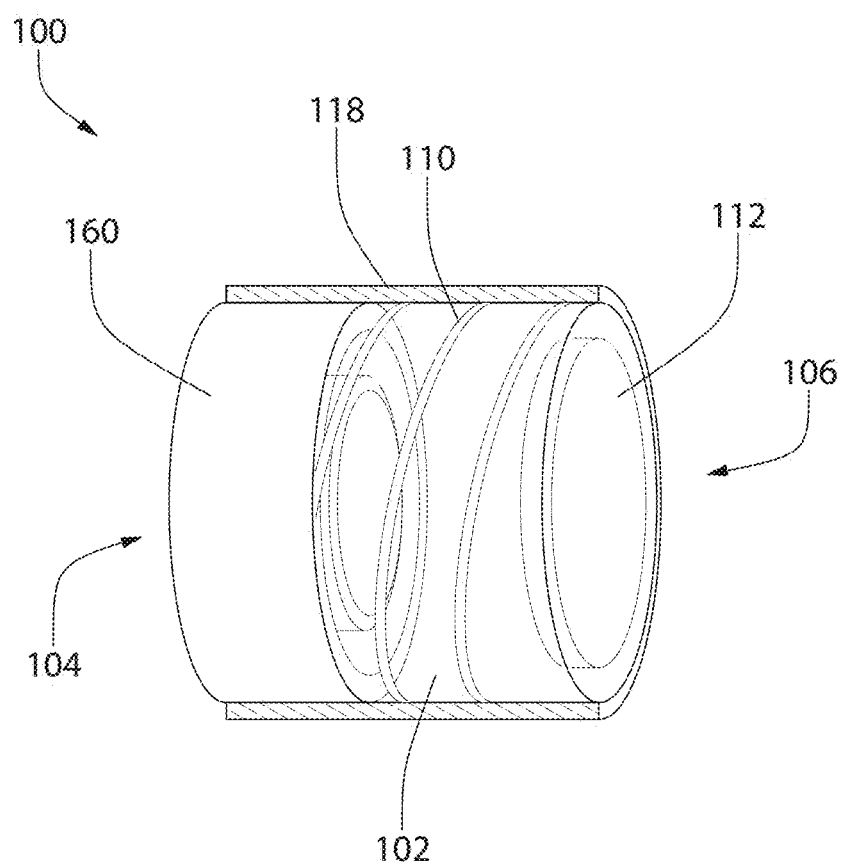
FIG. 17 depicts a side view of an exemplary lamprey lock device of the present invention comprising a media valve.
Figure 18:
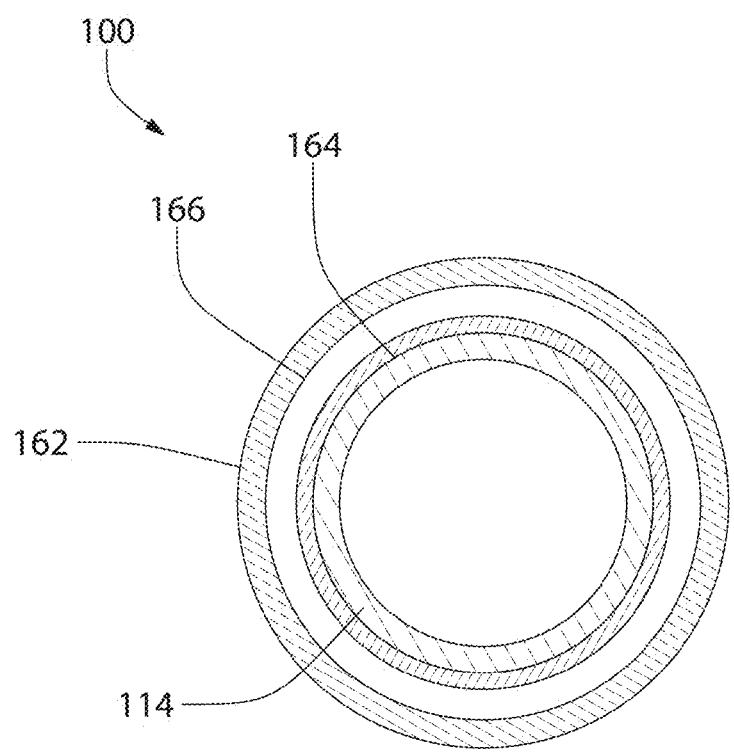
FIG. 18 depicts a coronal view of an exemplary lamprey lock device of the present invention comprising a media valve.
Figure 19:
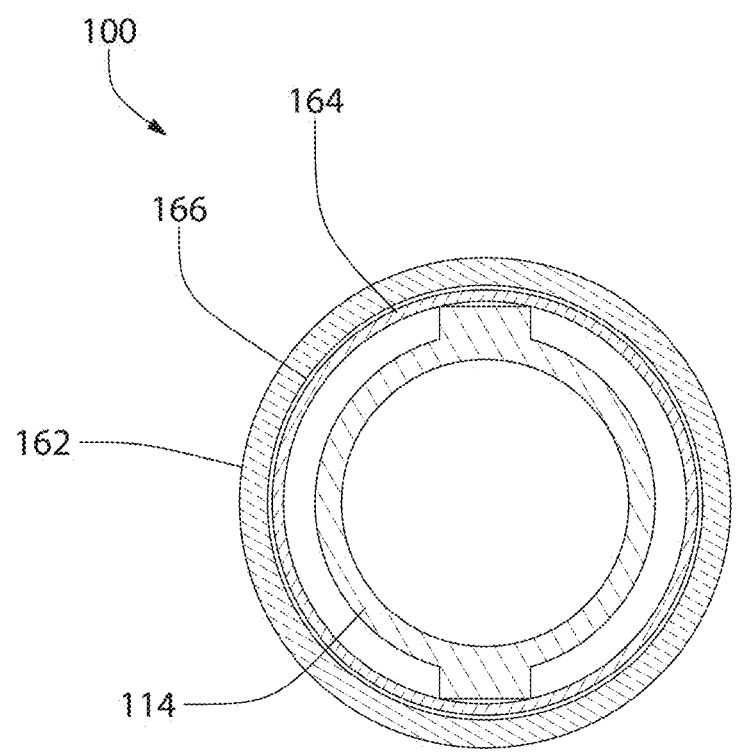
FIG. 19 depicts a coronal view of an exemplary lamprey lock device of the present invention comprising a media valve.

Referring now to FIG. 17, a side view of an exemplary lamprey lock device 100 of the present invention is shown. In one embodiment, lamprey lock device 100 may further comprise media valve 160 positioned at proximal end 104, configured to create an additional watertight seal around the medical device including but not limited to a catheter. In one embodiment, media valve 160 is configured to create an additional watertight seal in the event the user has not fully tightened the medical device attached to proximal end 104. In one embodiment, media valve 160 may be made from materials including but not limited to rubber, silicone and etc. In one embodiment, media valve 160 has an inner diameter ranging between 5-8 mm. In one embodiment, covering 118 is positioned around luer taper adapter 102 and media valve 160 to secure them together. Referring now to FIG. 18 and FIG. 19, a top view of an exemplary catheter 114 connection with luer taper adapter 102 comprising media valve 160 is shown. Media valve 160 comprises an outer surface 162, an inner surface 164 and a media chamber 166 positioned in between. Media chamber 166 may be inflated to seal create a watertight seal around catheter 114. In one embodiment, media chamber 166 may be inflated with any suitable media known to one skilled in the art including but not limited to water, saline, air, etc. In one embodiment, media chamber 166 may be filled with media by any suitable method known to one skilled in the art including but not limited to tubing, etc. Inner surface 164 may be compressed to allow insertion of catheter 114 into luer taper adapter 102. In one embodiment, media chamber 166 may be inflated and deflated to allow insertion and removal of catheter 114 from luer taper adapter 102.

Figure 20:
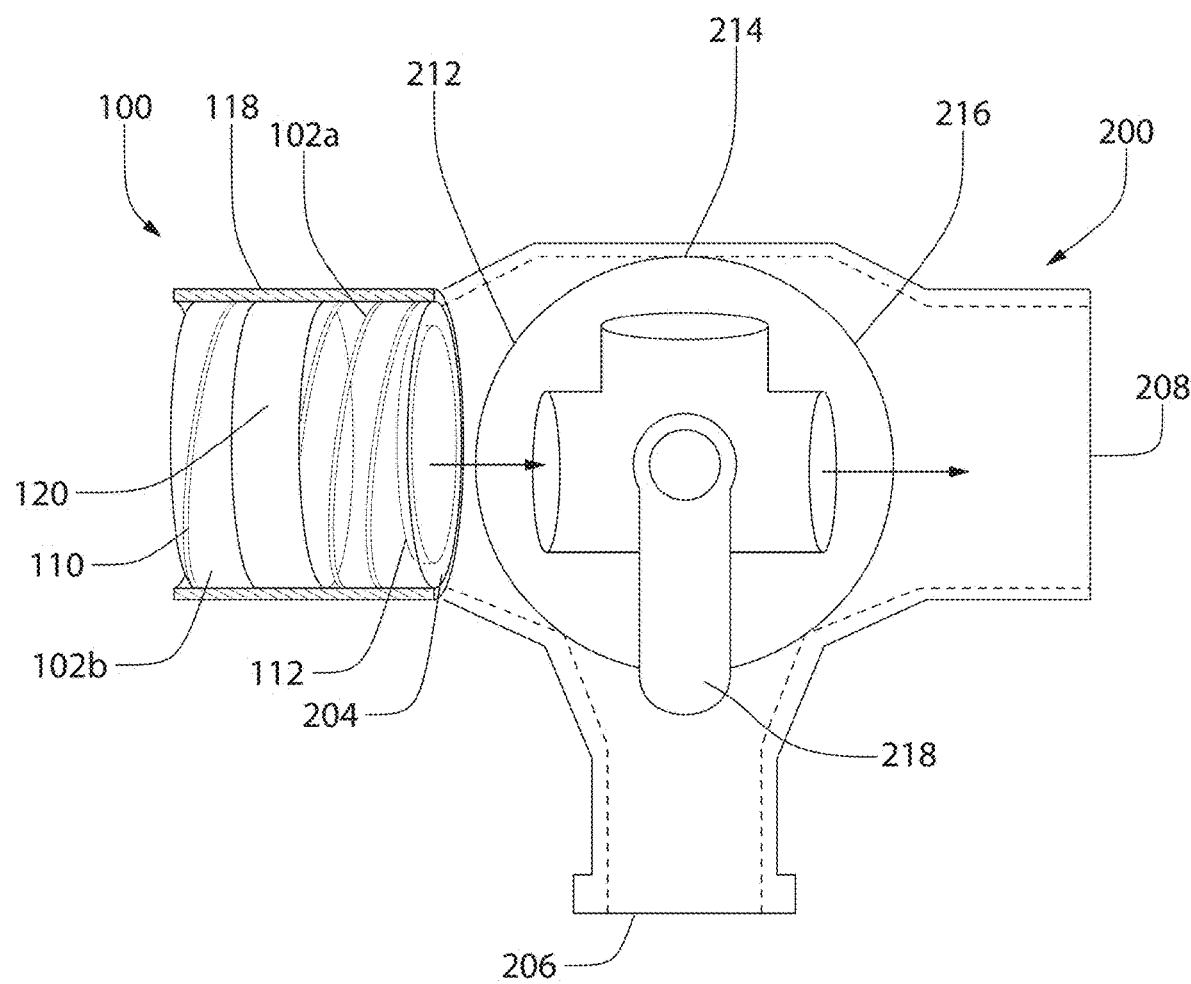
FIG. 20 depicts a side view of an exemplary lamprey lock device of the present invention comprising a three-way stopcock, wherein the configuration allows fluid connection between a connected catheter to the drainage reservoir.

Referring now to FIG. 20, in one embodiment, lamprey lock device 100 may be connected to a three-way stopcock 200. Three-way stopcock 200 comprises a tubular shape comprising a first tube section, a second tube section and a third tube section, each tube having a lumen defined by a circumference, and each tube section fluidly joined to each other at a central connector. The first tube section terminates in an open end 204 opposite to the central connector, the second tube section terminates in an open end 206 opposite to the central connector, and the third tube section terminates in an open end 208 opposite to the central connector. Stopcock 200 enables fluid communication between drainage reservoir and flush reservoir with single lumen catheters by selectively switching fluid access between a catheter with a drainage reservoir and a flush reservoir. The single lumen catheter is thereby configured to act as both a flush lumen and a drainage lumen. In one embodiment, the catheter is any standard drainage catheter known in the art.

Open end 204 is fluidly connected to distal end 106 of lamprey lock device 100 as described elsewhere herein. In one embodiment, open end 204 has the same diameter as lumen 108 of lamprey lock device 100.

In one embodiment, open end 206 is fluidly connected to a flush syringe. In one embodiment, open end 206 is fluidly connected to a flush pump. In one embodiment, open end 206 comprises a female luer adapter side port to allow insertion and withdrawal of fluids. In one embodiment, open end 208 is fluidly connected to a drainage reservoir. In one embodiment, the fluid connections can be any suitable mechanism known in the art configured to fluidly join tubes end-to-end, including but not limited to luer locks, tube fittings, threaded connectors, barbed connectors, and the like.

In one embodiment, direction of fluid flow in stopcock 200 can be adjusted manually. In one embodiment, direction of fluid flow in stopcock 200 can be adjusted electronically.

In one embodiment, stopcock 200 further comprises a central component 210 positioned within the central connector. Central component 210 comprises a circumference that is slightly less than the circumference of stopcock 200. As such, central component 210 may be inserted within stopcock 200 with minimal clearance. When inserted within stopcock 200, the minimal tolerance between the outer surface of central component 210 and the inner surface of stopcock 200 prevents fluid from leaking to drainage reservoir or flush reservoir. Central component 210 comprises a first open side 212, a second open side 214, a third open side 216 and a closed side 218 and is provided to allow directional adjustment to the fluid pathway. In one exemplary embodiment shown in FIG. 20, first open side 212 is in alignment with open end 204, wherein second open side 214 is faced to the wall of stopcock 200, third opening 216 is in alignment with open end 208 and closed side 218 is in alignment with open end 206. In this exemplary configuration, central component 210 allows fluid connection between a connected catheter to open end 204 and a drainage reservoir and blocks fluid communication from the flush reservoir to the catheter.

Figure 21:
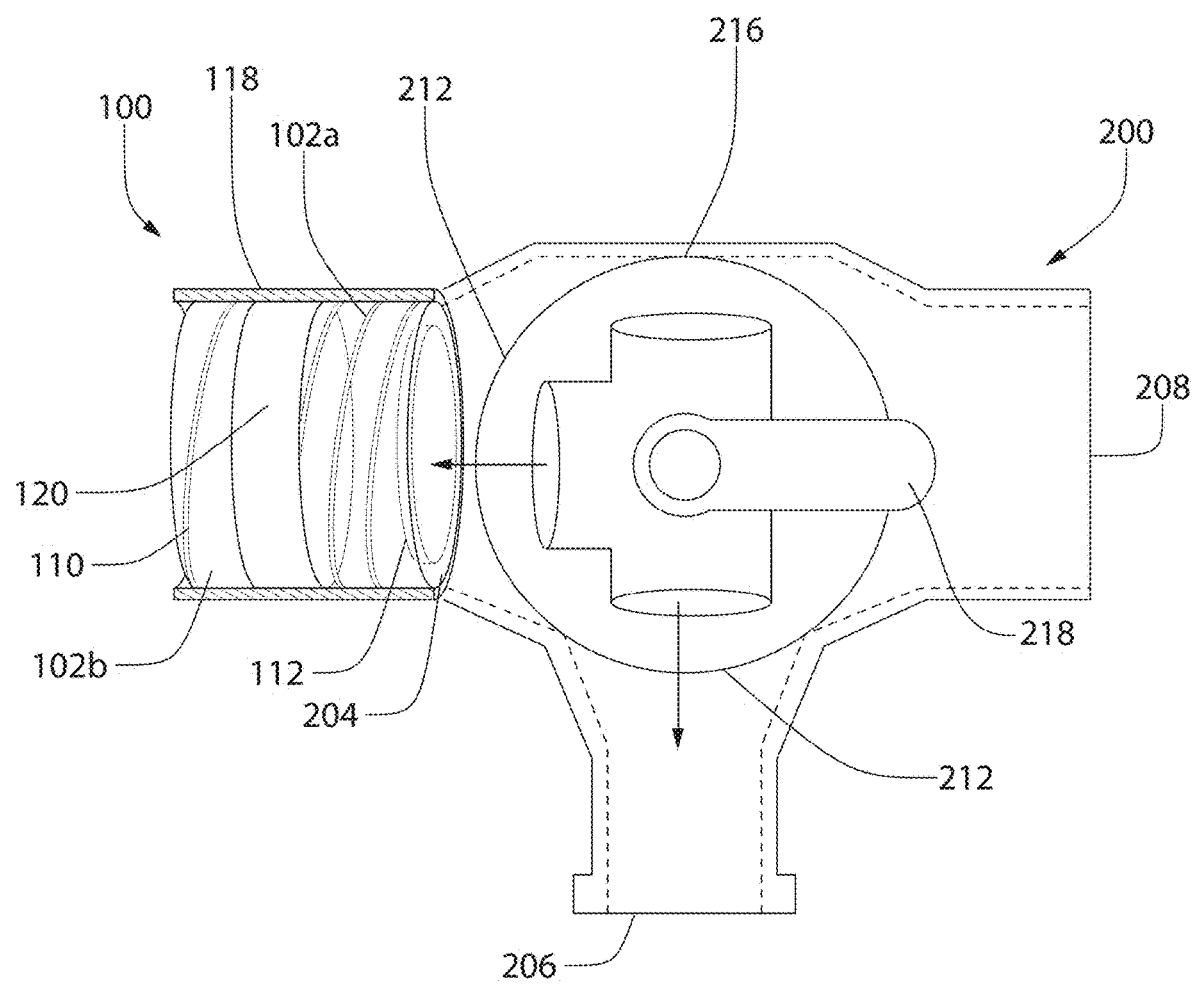
FIG. 21 depicts a side view of an exemplary lamprey lock device of the present invention comprising a three-way stopcock, wherein the configuration allows fluid connection between a connected catheter and the flush reservoir.

In operation, stopcock 200 comprises a drain mode and a flush mode. In the drain mode (depicted in FIG. 20), central component 210 produces a patent channel from the catheter through first open side 212 and third open side 216 into a drainage reservoir, while closed side 218 blocks fluid communication to a flush reservoir. In flush mode (as depicted in FIG. 21), central component 210 produces a patent channel from the flush reservoir through first open side 212 and second open side 214 into the catheter connected to lamprey lock device 100, while closed side 218 blocks fluid communication to the drainage reservoir. Central component 210 can be controlled manually or electronically to switch stopcock 200 between the drain mode and the flush mode.

Figure 22:
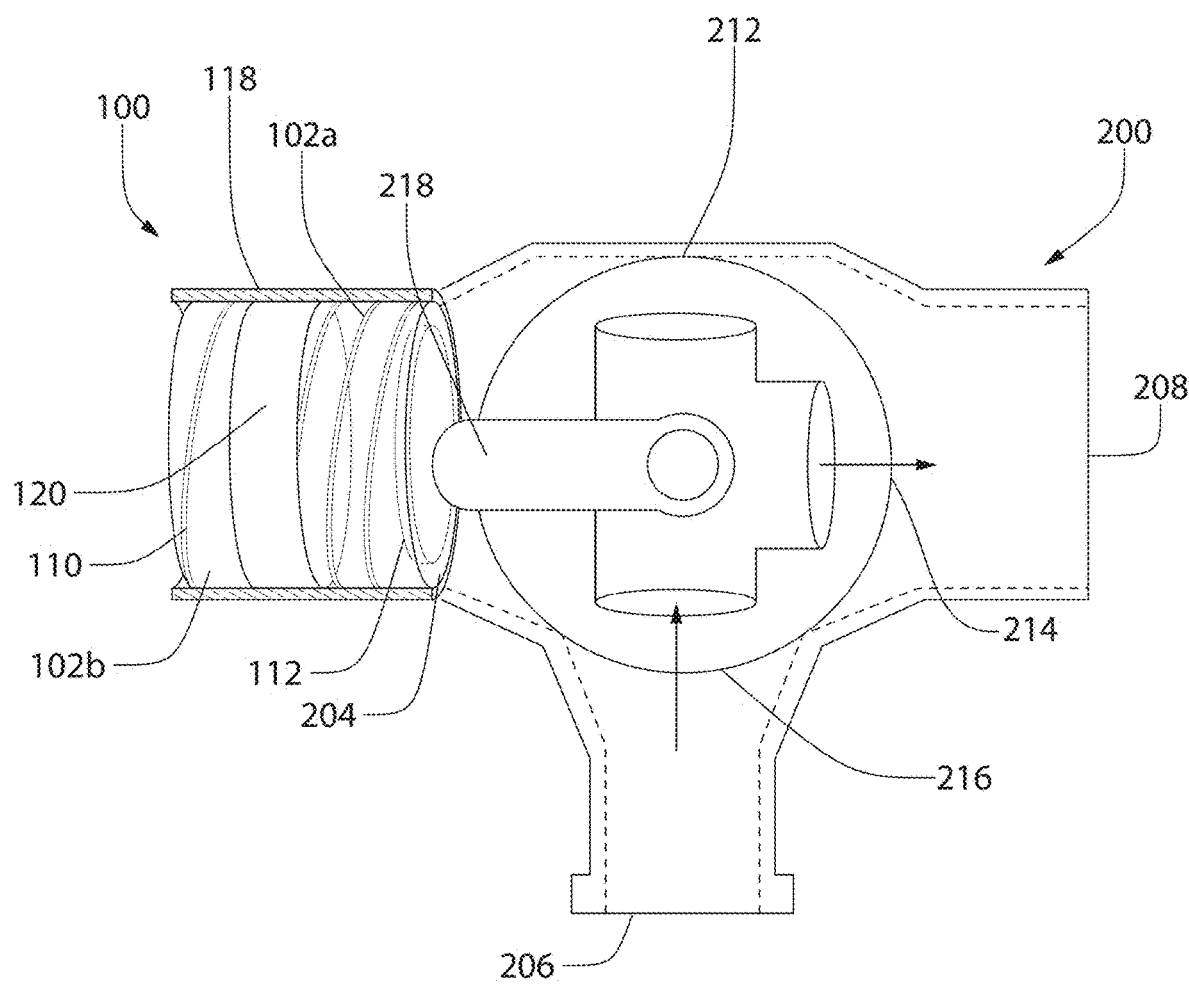
FIG. 22 depicts a side view of an exemplary lamprey lock device of the present invention comprising a three-way stopcock, wherein the configuration allows fluid connection between the flush reservoir and the drainage reservoir.

Stopcock 200 may also produce a patent channel from the flush reservoir to drainage reservoir through second open side 214 to third open side 216 as shown in FIG. 22.

Figure 23:
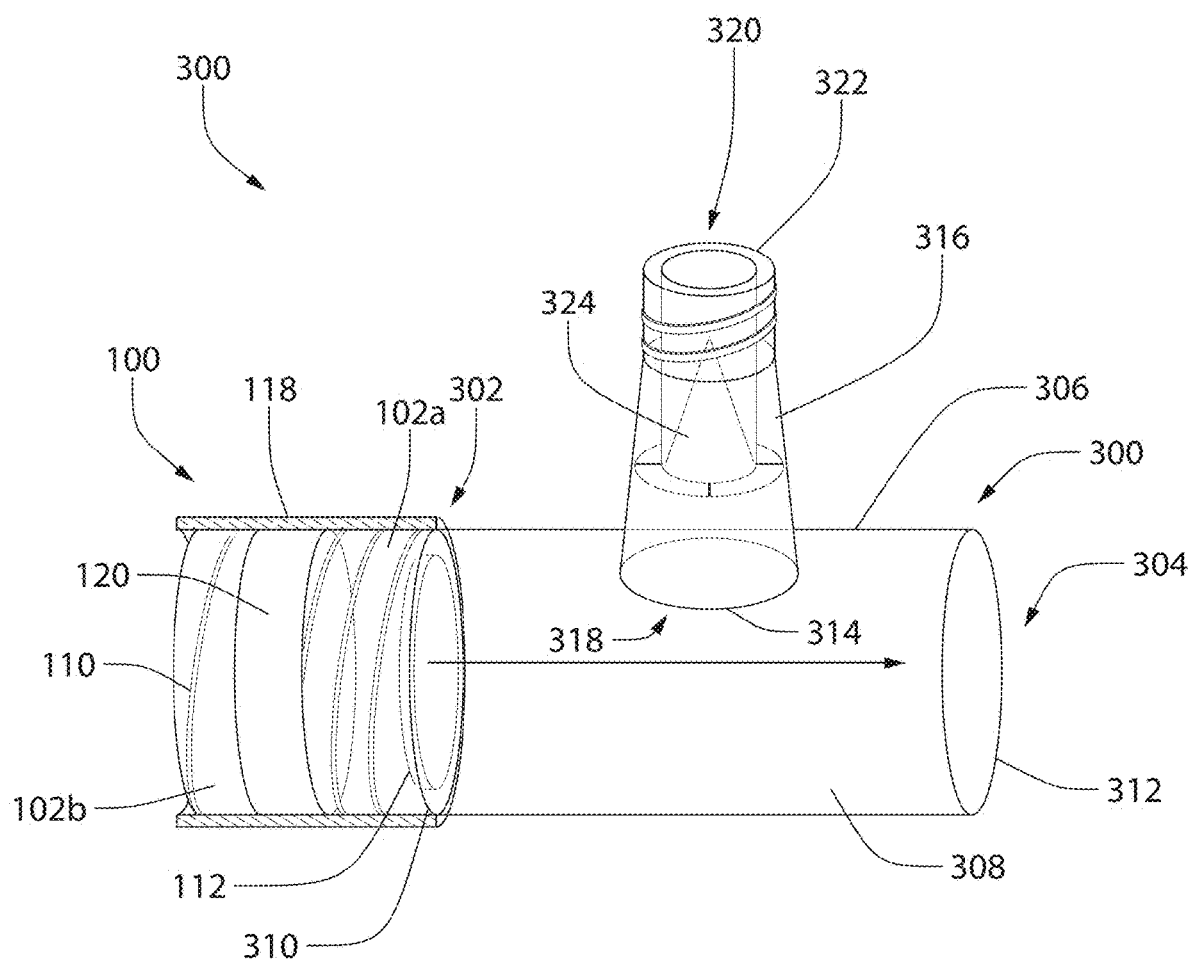
FIG. 23 depicts an exemplary lamprey lock device of the present invention comprising a compressible side port valve in a close position.

Referring now to FIG. 23, in one embodiment, lamprey lock device 100 may be connected to a tubing 300 at distal end 106, wherein tubing 300 comprises a proximal end 302, a distal end 304 and a body 306 therebetween. Body 306 has an elongated cylindrical shape comprising a lumen 308 with a diameter ranging between 2-5 mm. In one embodiment, body 306 is approximately 5-16 mm in length, however any suitable length may be used. Body 306 has a first opening 310 at proximal end 302, a second opening 312 at distal end 304 and a third opening 314. In one embodiment, third opening 314 is located between first opening 310 and second opening 312 at any suitable distance away from first opening 310 and second opening 312. In one embodiment, the distance between first opening 310 and third opening 314 is more than the distance between the second opening 312 and the third opening 314. In one embodiment, the distance between first opening 310 and third opening 314 is less than the distance between the second opening 312 and the third opening 314. In one embodiment, first opening 310 and second opening 312 have an inner diameter ranging between 4-5 mm. In one embodiment, third opening 314 has a diameter ranging between 2-5 mm.

First opening 310 is fluidly connected to distal end 106 of lamprey lock device 100 as described elsewhere herein. In one embodiment, first opening 310 has the same diameter as lumen 108 of lamprey lock device 100.

Second opening 312 is fluidly connected to a drainage reservoir. In one embodiment, the fluid connections can be any suitable mechanism known in the art configured to fluidly join tubes end-to-end, including but not limited to luer locks, tube fittings, threaded connectors, barbed connectors, and the like.

Body 306 further comprises a side port 316. Side port 316 is fluidly connected to body 306 through third opening 314. In one embodiment, side port 316 has an angle ranging between 20-90 degrees with respect to body 306.

Side port 316 comprises a first end 318, a second end 320 and a lumen therebetween. Second end 320 comprises an opening 322. In one embodiment, opening 322 may have the same diameter as third opening 314. In one embodiment, opening 322 may have a larger diameter as third opening 314. In one embodiment, opening 322 may have a smaller diameter than third opening 314. In one embodiment, opening 322 is sized and configured to connect to standard sizing for luer connectors, such as those that meet ANSI standards. In one embodiment, opening 322 may be fluidly connected to a syringe 323.

Side port 316 further comprises a valve member configured to allow selective fluid communication between body 306 and side port 316, wherein the valve member comprises a compressible component 324, a support structure 326 and at least one channel 328.

Figure 24:
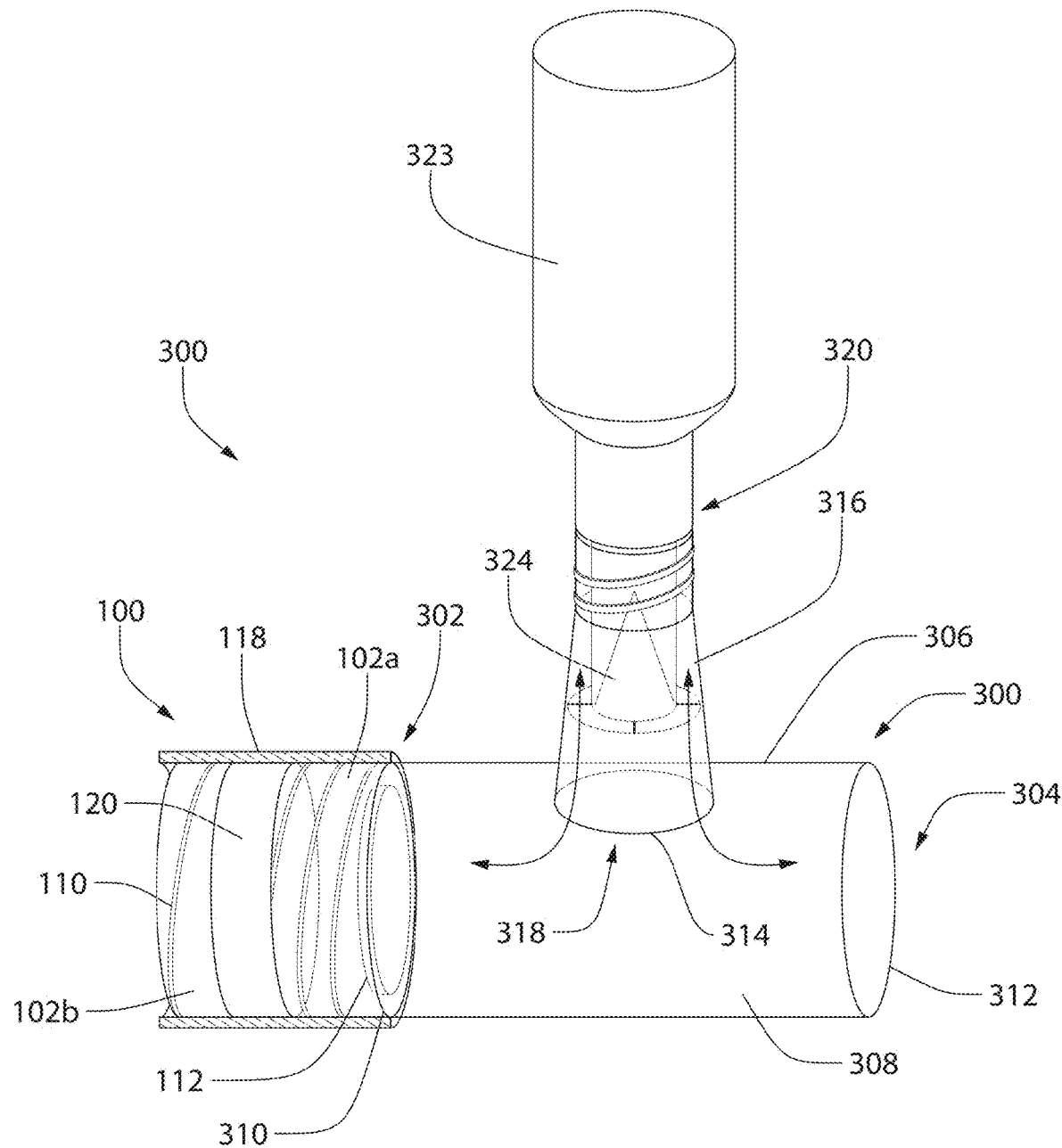
FIG. 24 depicts an exemplary lamprey lock device of the present invention comprising a compressible side port valve in an open position.

Compressible component 324 is configured to receive the luer tip of syringe 323 at second end 320 (FIG. 24). Once syringe 323 is inserted, the luer tip pushes compressible component 324 down which in turn causes at least one channel 328 to open and allow fluid communication between side port 316 and body 306. Once syringe 324 is unplugged, compressible component 324 springs back to its original position, such that a fluid tight seal is once again formed at the at least one channel 328.

Side port 316 further comprises a support structure 326. Support structure 326 is configured to guide compressible component 324 through its travel. In one embodiment, support structure 326 maintains proper alignment of compressible component 324 within the valve member which ensures leak free flow performance.

In one embodiment, body 306 and side port 316 may be constructed from a flexible plastic material. In one embodiment, body 306 may be made from a polymeric material, such as silicone, nylon, or urethane. Any medically acceptable thermoplastic or thermoset material may be used, including PTFE, a fluoropolymer, polyethylene, polypropylene, acetal, urethane, and others, however, it may be constructed from any material known to one skilled in the art. In one embodiment, body 306 may be made from a flexible material so that it is bendable throughout its length and at least at first opening 310, second opening 312 and third opening 314. In one embodiment, side port 316 may be made from a flexible material so that it is bendable throughout its length.

Figure 25:
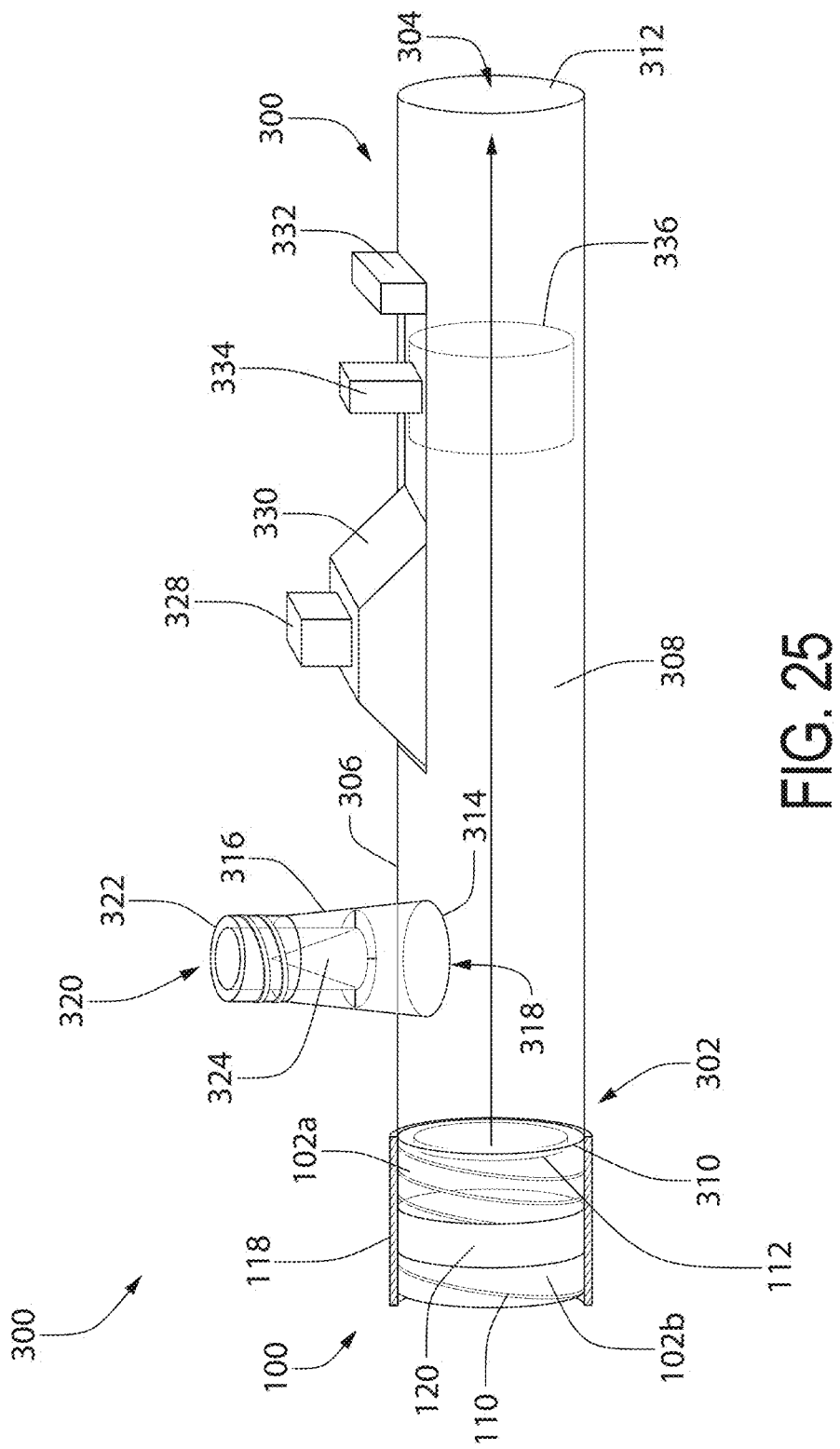
FIG. 25 depicts an exemplary lamprey lock device of the present invention comprising a compressible side port valve in a close position and a flow switch in an open position.

In one embodiment, tubing 300 may further comprise a flow switch 328 positioned on the external surface of body 306, configured to allow selective fluid communication between body 306 and drainage reservoir (FIG. 25). In one embodiment, flow switch 328 is positioned distal to side port 316.

Flow switch 328 comprises a tab 330, a track 332 configured to allow longitudinal movement of tab 330 between an open and close position, an occluding member 334 configured to move vertically and a compressible tubing 336.

Tab 330 may have a wide variety of shapes as known to one skilled in the art, including but not limited to cylindrical, prism-shaped, trapezoidal, square, or rectangular bars or beams, I-beams, elliptical beams, bowl-shaped surfaces, and others.

In operation, tab 330 is configured to move between an open and close position by slidably moving left and right on track 332. As tab 330 slides to the right on track 332, occluding member 334 is moved down vertically and pushes on compressible tubing 336. Applying a force to compressible tubing 336 causes flow restriction between body 308 and the drainage reservoir.

Figure 26:
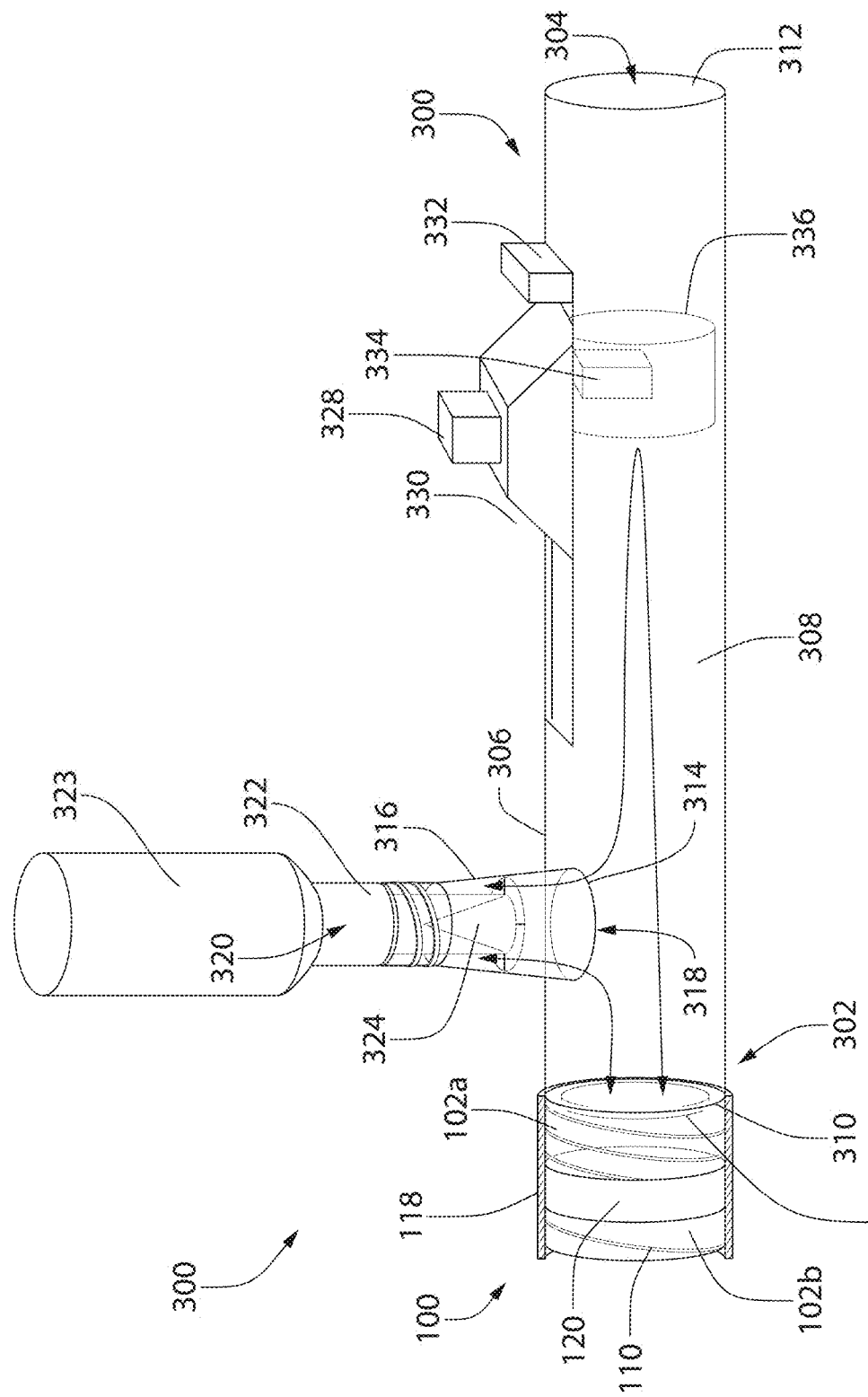
FIG. 26 depicts an exemplary lamprey lock device of the present invention comprising a compressible side port valve in an open position and a flow switch in a close position.

In one embodiment, if tab 330 is moved all the way to the right, occluding member 334 is pushed down completely, such that the fluid communication between body 306 and drainage reservoir is completely closed (FIG. 26). In one embodiment, tab 330 location may be placed anywhere in between the open and close position which in turn causes partial flow communication between body 306 and the drainage reservoir.

In one embodiment, compressible tubing 336 may be attached to distal end 304 of body 306. In one embodiment, compressible tubing 336 may have a length of approximately 4-4.5 mm. In one embodiment, compressible tubing 336 may be made from a polymeric material, such as silicone, nylon, or urethane. Any medically acceptable thermoplastic or thermoset material may be used, including PTFE, a fluoropolymer, polyethylene, polypropylene, acetal, urethane, and others, however, it may be constructed from any material known to one skilled in the art. In one embodiment, compressible tubing 336 may be made from any flexible material so that it is bendable throughout its length. In one embodiment, body 306 may be attached to compressible tubing 336 by any suitable mechanism known in the art configured to fluidly join tubes end-to-end, including but not limited to luer locks, tube fittings, threaded connectors, barbed connectors, and the like.

Figure 27:
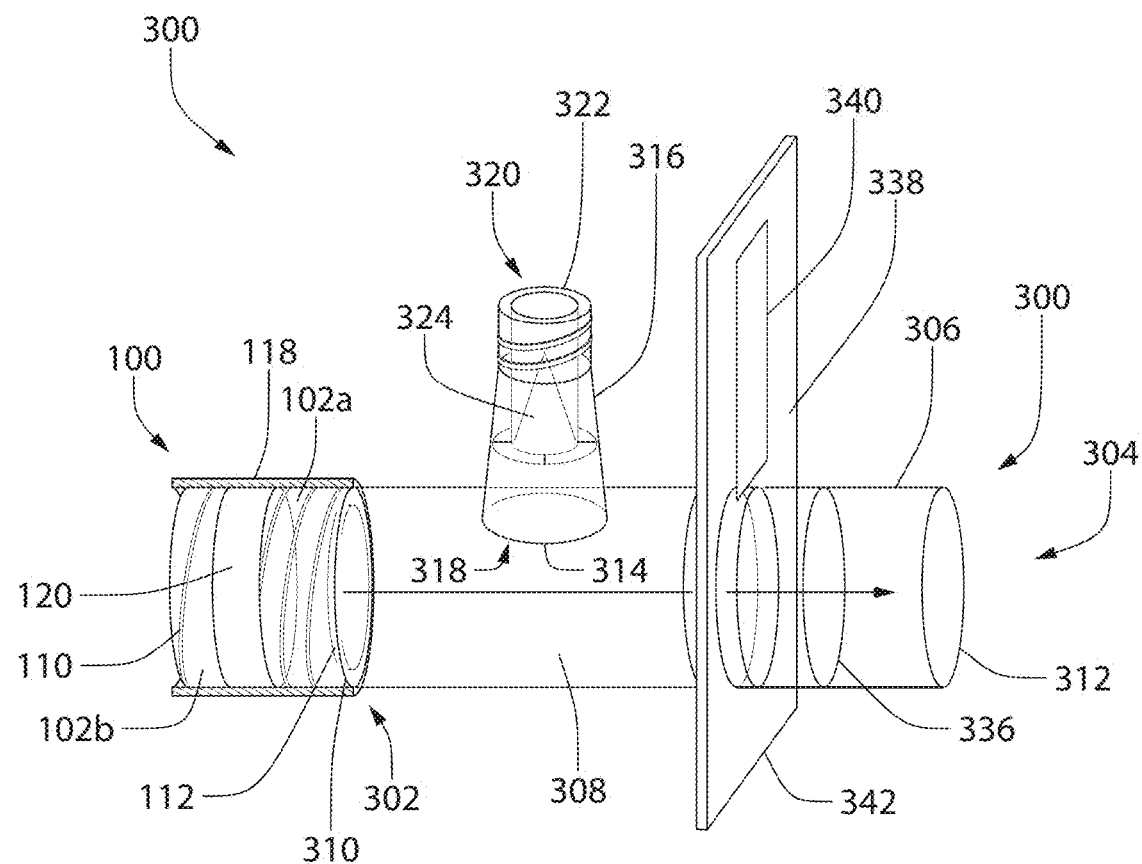
FIG. 27 depicts an exemplary lamprey lock device of the present invention comprising a compressible side port valve in a close position and an external clamp in an open position.
Figure 28:
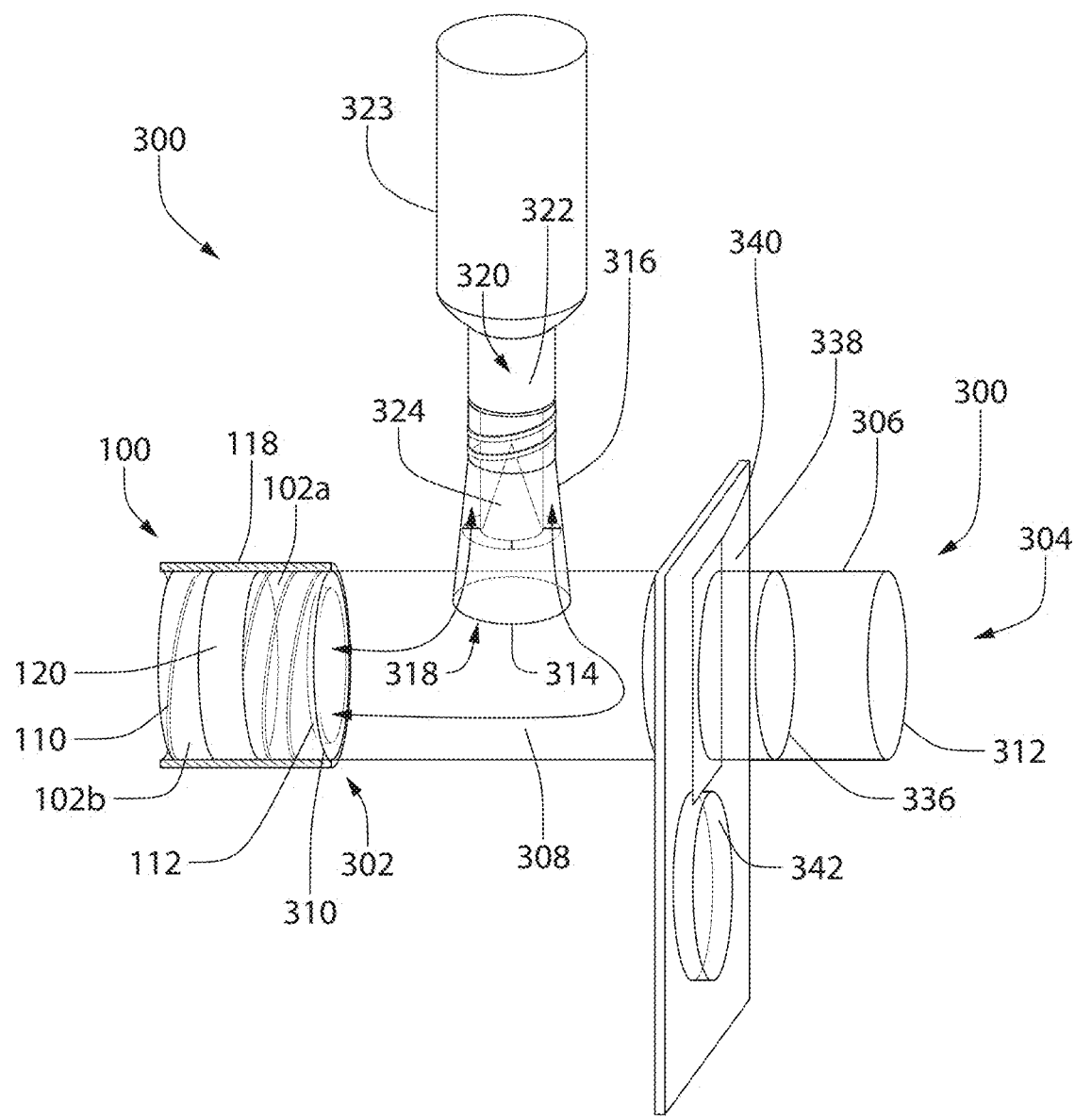
FIG. 28 depicts an exemplary lamprey lock device of the present invention comprising a compressible side port valve in an open position and an external clamp in a close position.

In one embodiment, tubing 300 may further comprise an external clamp 338 (FIG. 27) positioned distal to side port 316. External clamp 338 is connected to compressible tube 336 and thereby control the cross-sectional size of an opening in body 306, through which the fluid flows. External clamp 338 comprises a rounded opening 340 and an occluded slot 342. Rounded opening 340 has a diameter approximately equal or very slightly smaller than an exterior diameter of compressible tube 336. In one embodiment, the position of external clamp 338 along compressible tube 336 is adjustable by sliding external clamp along the length of compressible tube 336, while compressible tube 336 is located in rounded opening 340. The close size relationship of rounded opening 340 and the diameter of compressible tube 336 frictionally maintains external clamp 338 at a desired position along a length of compressible tube 336. When in rounded opening 340, compressible tube 336 is not occluded to inhibit the flow of fluid. Occluding slot 340 converges to create a narrow width into which compressible tube 336 is forced as shown in FIG. 28. When compressible tube 336 is forced into occluding slot 340, the sidewall of compressible tube 336 is pinched together, thereby occluding compressible tube 336 and preventing the flow of fluid from body 306 towards the drainage reservoir.

In one embodiment, external clamp 338 is a slide clamp. In one embodiment, external clamp 338 is a ramp or roller clamp. In on embodiment, external clamp 338 may be any other clamping mechanism known to one skilled in the art.

Figure 29:
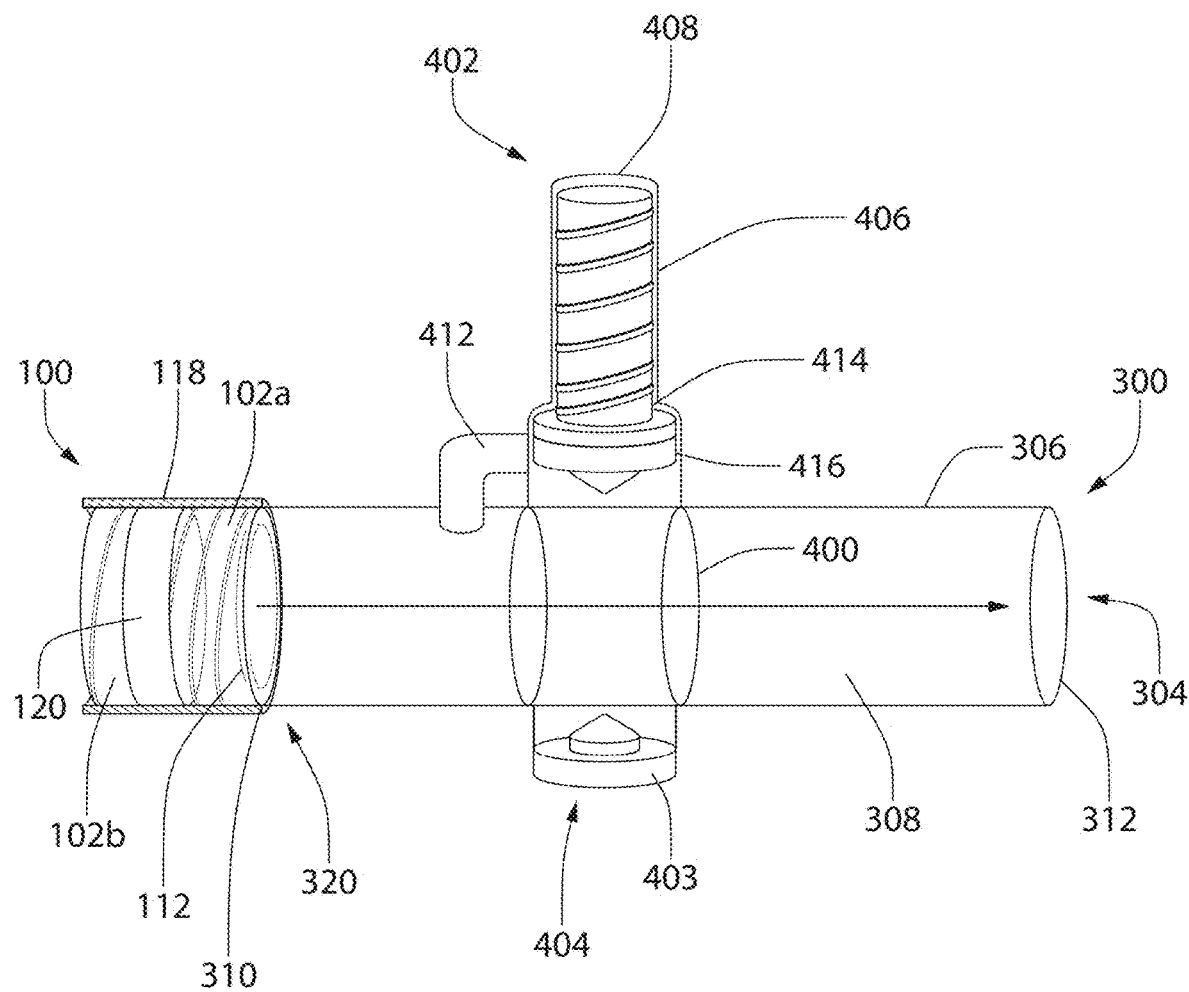
FIG. 29 depicts an exemplary lamprey lock device of the present invention comprising a chamber having a side port and a compressible valve, wherein the valve is in a close position.

Referring now to FIG. 29, in one embodiment, tubing 300 may further comprise a chamber 400 positioned anywhere between first opening 310 and second opening 312, configured to engage the exterior surface of body 306.

Figure 30:
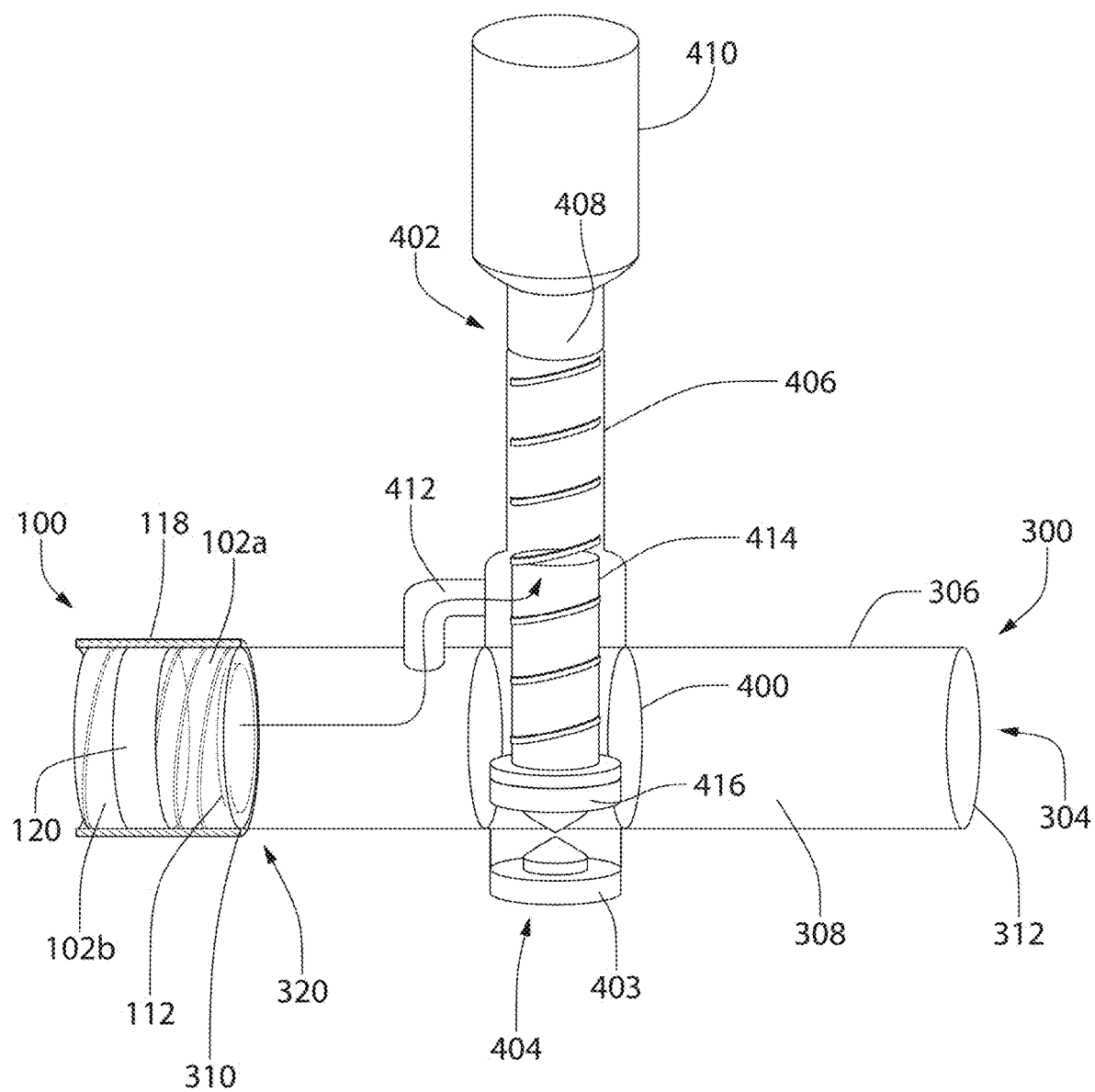
FIG. 30 depicts an exemplary lamprey lock device of the present invention comprising a chamber having a side port and a compressible valve, wherein the valve is in an open position.

Chamber 400 comprises a first end 402, a second end 404, a side port 406 positioned at first end 402 and a bottom part 403 positioned at second end 404. In one embodiment, side port 406 comprises an opening 408 at first end 402. In one embodiment, opening 408 is sized and configured to connect to standard sizing for luer connectors, such as those that meet ANSI standards. In one embodiment, opening 408 may be fluidly connected to a syringe 410 (FIG. 30).

Side port 406 is fluidly connected to body 306 through a side channel 412. In one embodiment, side channel 412 has a diameter ranging between 2-5 mm. In one embodiment, side channel 412 may be any shape including but not limited to a L-shape tubing.

Side port 406 further comprises a valve member configured to allow selective fluid communication between body 306 and side port 406, wherein the valve member comprises a compressible component 414 and a tip 416 positioned below compressible component 414. Compressible component 414 is configured to receive the luer tip of syringe 410. Once syringe 410 is inserted, the luer tip pushes compressible component 414 down on body 306 all the way to bottom part 403, which in turn causes side channel 412 to open and allow fluid communication between side port 406 and body 306 and blocks fluid communication between catheter at first opening 310 and the drainage reservoir at second opening 312. Once syringe 410 is unplugged, compressible component 414 springs back to its original position, such that a fluid tight seal is once again formed between side port 406 and body 306.

In one embodiment, tip 416 is a pointed tapered tip. In one embodiment, tip 416 is a pointed tapered tip of at least 45 degrees to allow improved compression. In one embodiment, bottom part 403 also comprises a tapered component. In one embodiment, bottom part 403 comprises a pointed tapered tip of at least 45 degrees.

Figure 31:
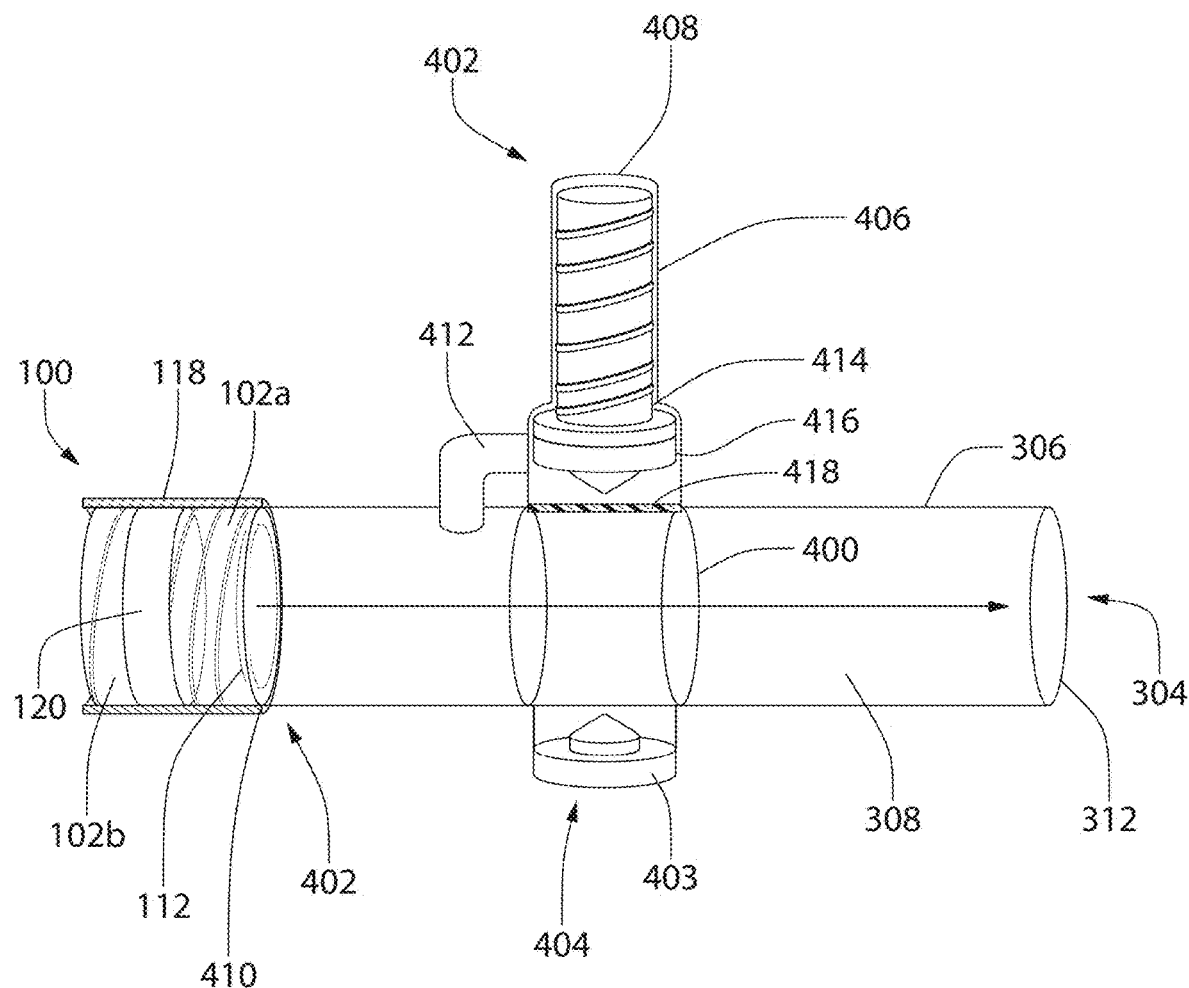
FIG. 31 depicts an exemplary lamprey lock device of the present invention comprising a membrane within the chamber having a side port and a compressible valve, wherein the valve is in a close position.
Figure 32:
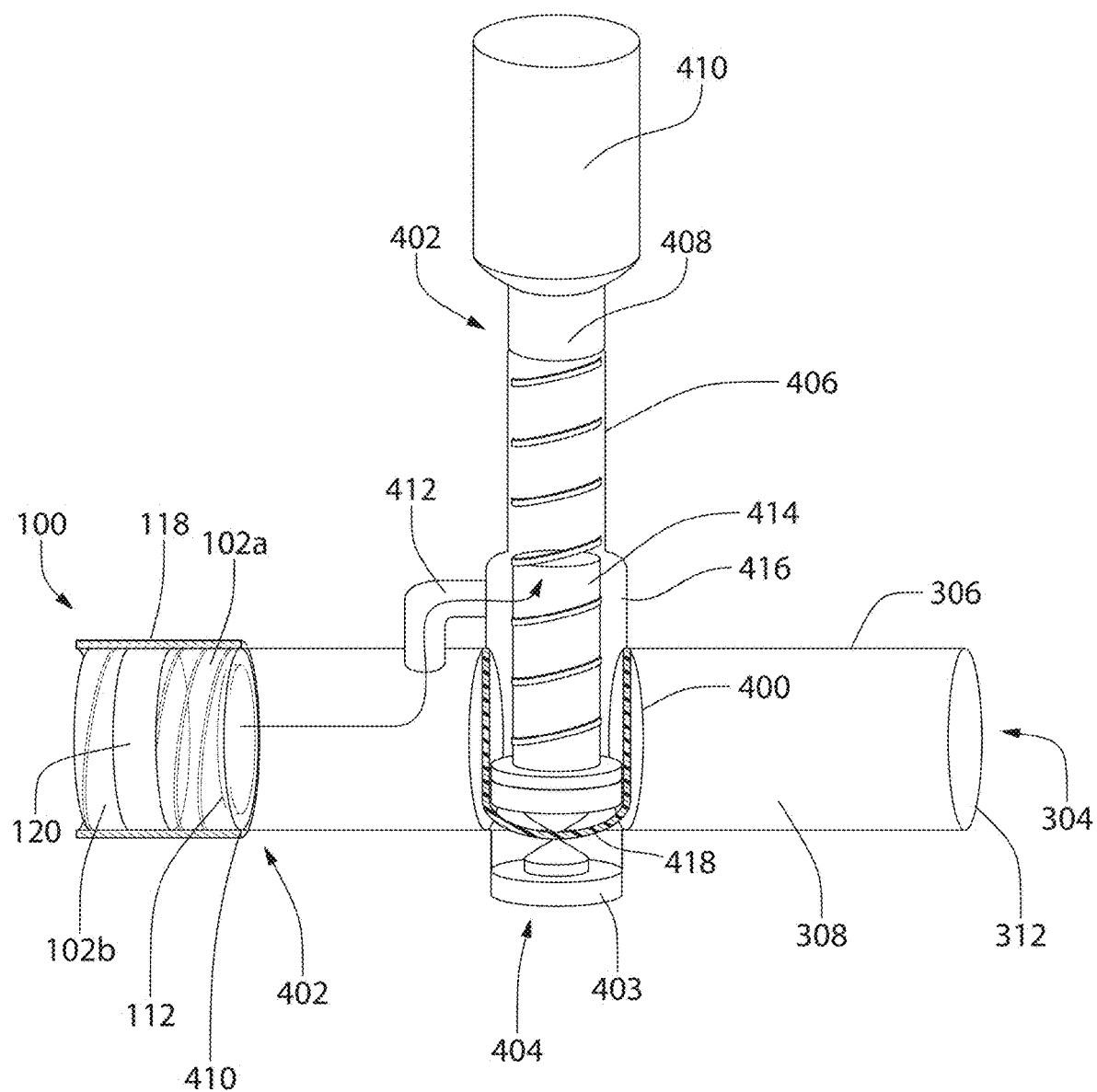
FIG. 32 depicts an exemplary lamprey lock device of the present invention comprising a membrane within the chamber having a side port and a compressible valve, wherein the valve is in an open position.

Referring now to FIG. 31 and FIG. 32, in one embodiment, chamber 400 further comprises a compressible membrane 418 positioned below tip 416 and over body 306. Compressible membrane 418 is configured to prevent fluid flow into inferior part of chamber 400 when valve member is in open position.

Figure 33:
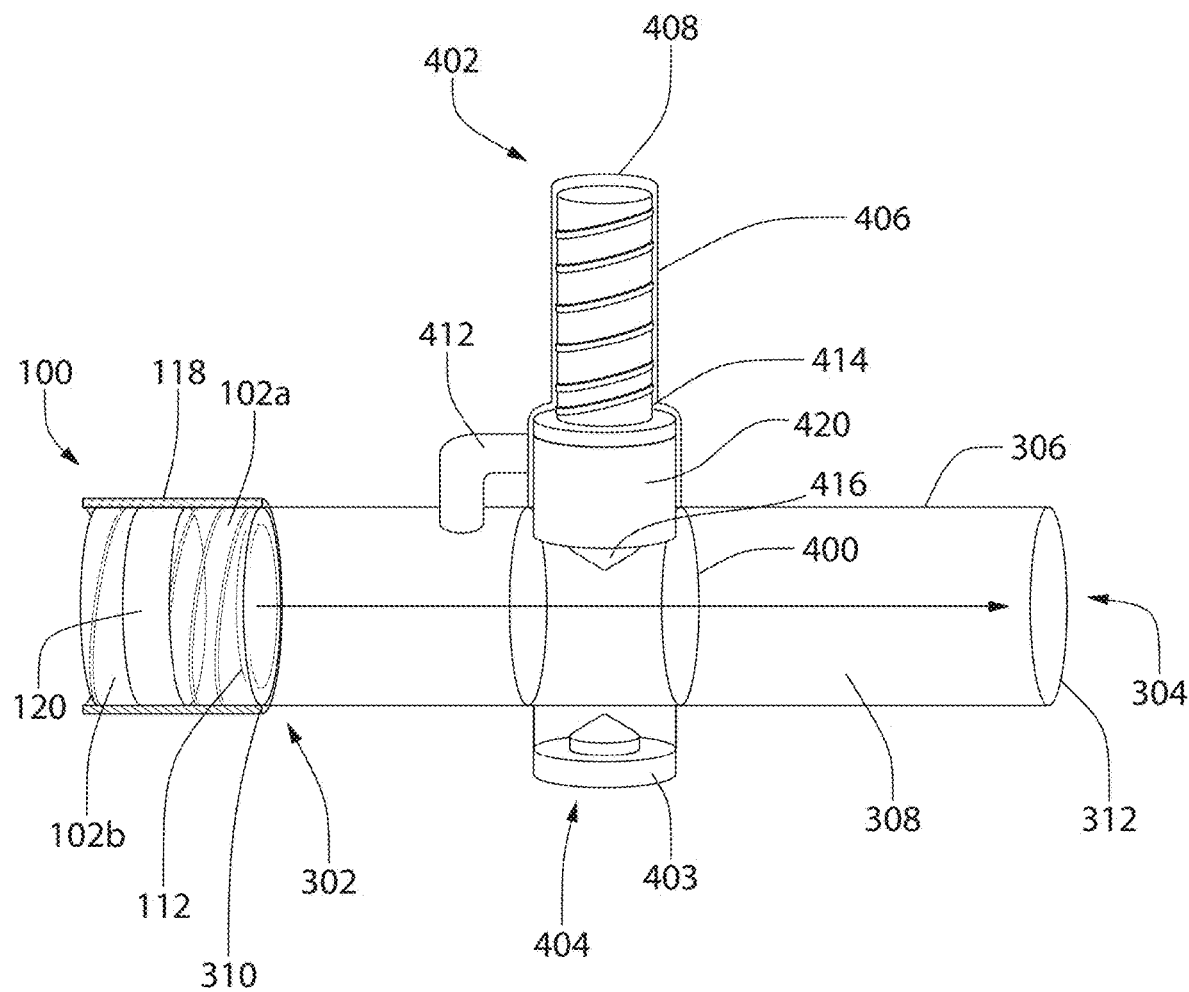
FIG. 33 depicts an exemplary lamprey lock device of the present invention comprising a side port valve stopping flow, wherein the valve is in a close position.
Figure 34:
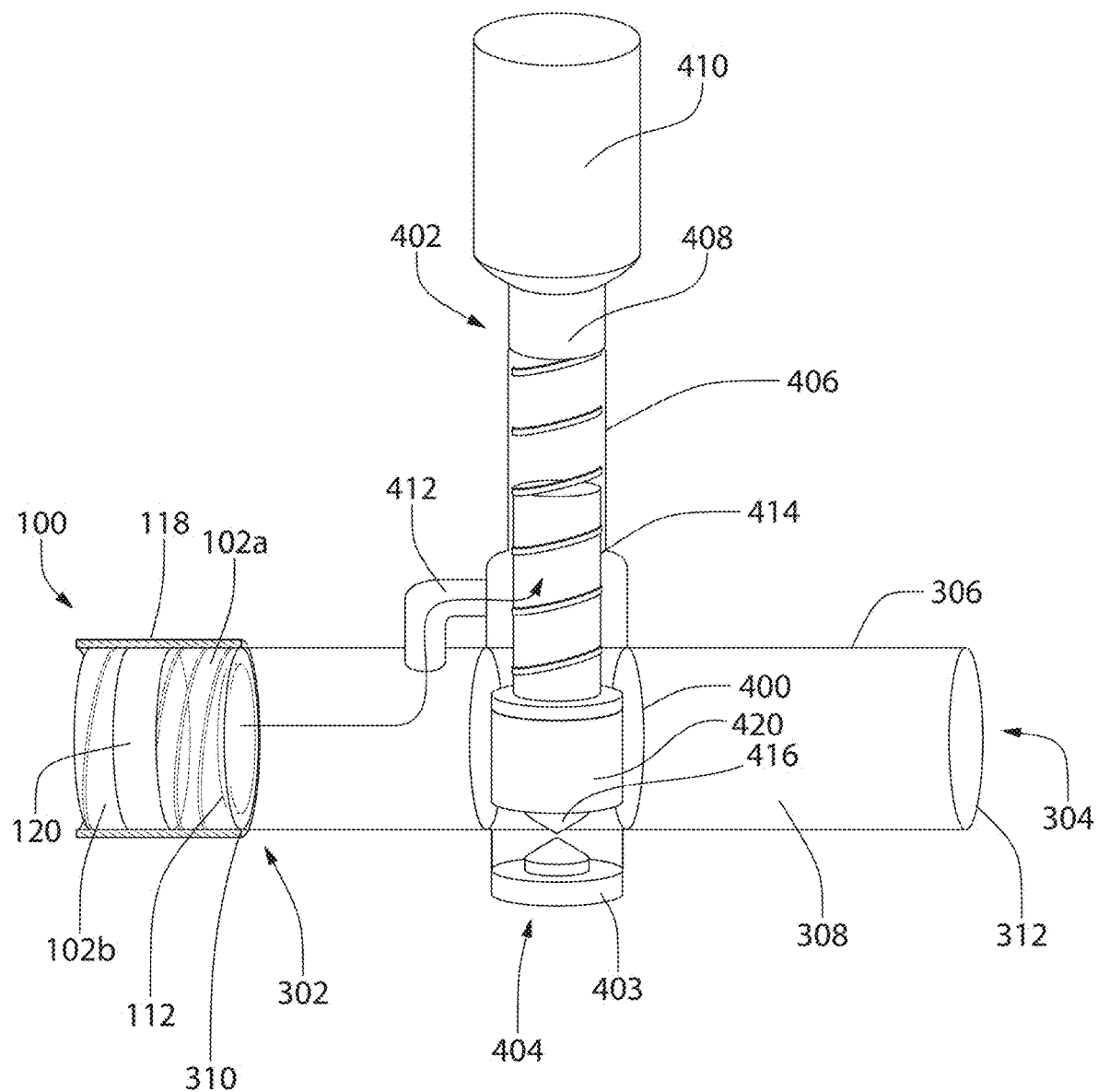
FIG. 34 depicts an exemplary lamprey lock device of the present invention comprising a side port valve stopping flow, wherein the valve is in an open position.

Referring now to FIG. 33, in one embodiment, tip 416 may comprise a base 420, configured to be wide enough to block flow into chamber 400 while in the closed position. Referring now to FIG. 34, once syringe 410 is inserted, the luer tip pushes compressible component 414 down on body 306 all the way to bottom part 403, which in turn causes base 420 to move down and unblocks the opening to side channel 412 and allow fluid communication between side port 406 and body 306 and blocks fluid communication between catheter at first opening 310 and the drainage reservoir at second opening 312.

Method of Use

The present invention also relates to methods for fluid transfer between two devices or objects by maximizing the inner diameter of connections between two objects or devices including but not limited to a catheter, tubing, veress needles, trocars, syringes, or gas/fluid delivery systems. In one embodiment, the present invention also relates to methods of providing a connection between a catheter at its proximal end to a tubing including but not limited to a drainage reservoir tubing to allow flushing and draining fluid from a body cavity.

Figure 35:
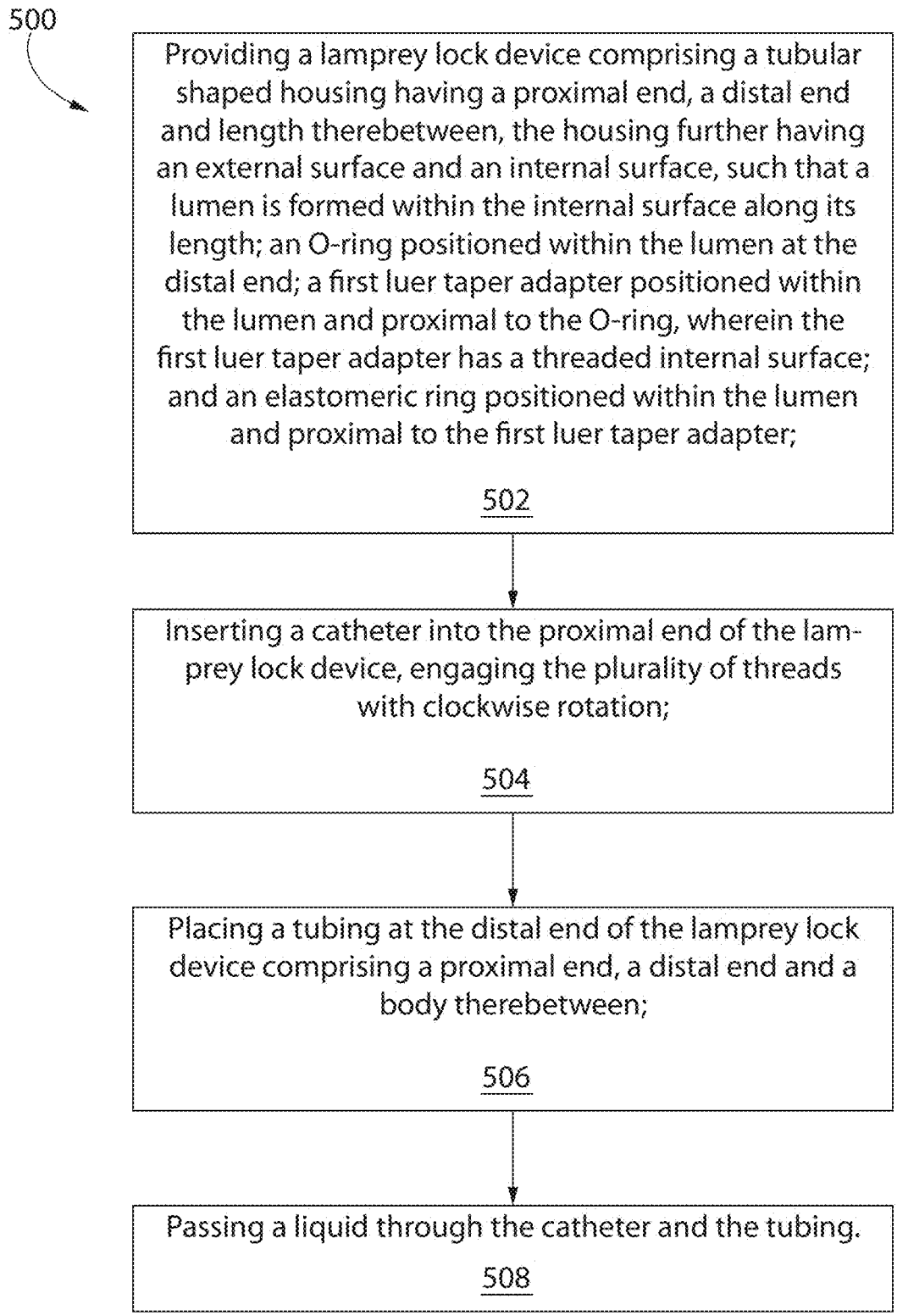
FIG. 35 is a flowchart depicting an exemplary method of using the lamprey lock device of the present invention.

Referring now to FIG. 35, an exemplary method 500 of draining a body cavity is depicted. Method 500 begins with steps 502, wherein a lamprey lock device comprising a luer taper adapter having a proximal end, a distal end and a lumen therebetween, wherein the lumen comprises a plurality of threads within its interior wall; a circumferential elastomeric seal positioned at the proximal end of the luer taper adapter, configured to create a watertight seal with a proximal end of an inserted catheter; and a covering positioned around the luer taper adapter and the circumferential elastomeric seal, configured to secure the luer tap adapter and the circumferential elastomeric seal together is provided. In step 504, a catheter is inserted into the proximal end of the lamprey lock device, engaging the plurality of threads with clockwise rotation. In one embodiment, the clockwise rotation creates a watertight seal with the O-ring at the distal end. In step 506, a tubing is placed at the distal end of the lamprey lock device comprising a proximal end, a distal end, and a body therebetween. In step 508, a liquid is passed through the catheter and the tubing. In one embodiment, this connection may allow a liquid from a body cavity to be drained from the catheter to a drainage reservoir connected to the distal end of the tubing.

In one embodiment, the lamprey lock device of the present invention may be attached to a three-way stopcock. In one embodiment, the tubing may further comprise a side port fluidly connected to the body, wherein the side port comprises a first end, a second end and a lumen therebetween and is configured to be connected to standard sizing for luer connectors at second end and allow selective fluid communication between the body and the side port. In one embodiment, the tubing may further comprise a flow switch positioned on the external surface of the body and distal to the side port, configured to allow selective fluid communication between the body and the drainage reservoir. In one embodiment, the tubing may further comprise an external clamp positioned on the external surface of the body and distal to the side port, configured to allow selective fluid communication between the body and the drainage reservoir.

EXPERIMENTAL EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art may, using the preceding description and the following illustrative examples, make and utilize the compounds of the present invention and practice the claimed methods. The following working examples therefore specifically point out exemplary embodiments of the present invention and are not to be construed as limiting in any way the remainder of the disclosure.

Example 1: Lamprey Lock Flow Data

Experimental Setup

Figure 36:
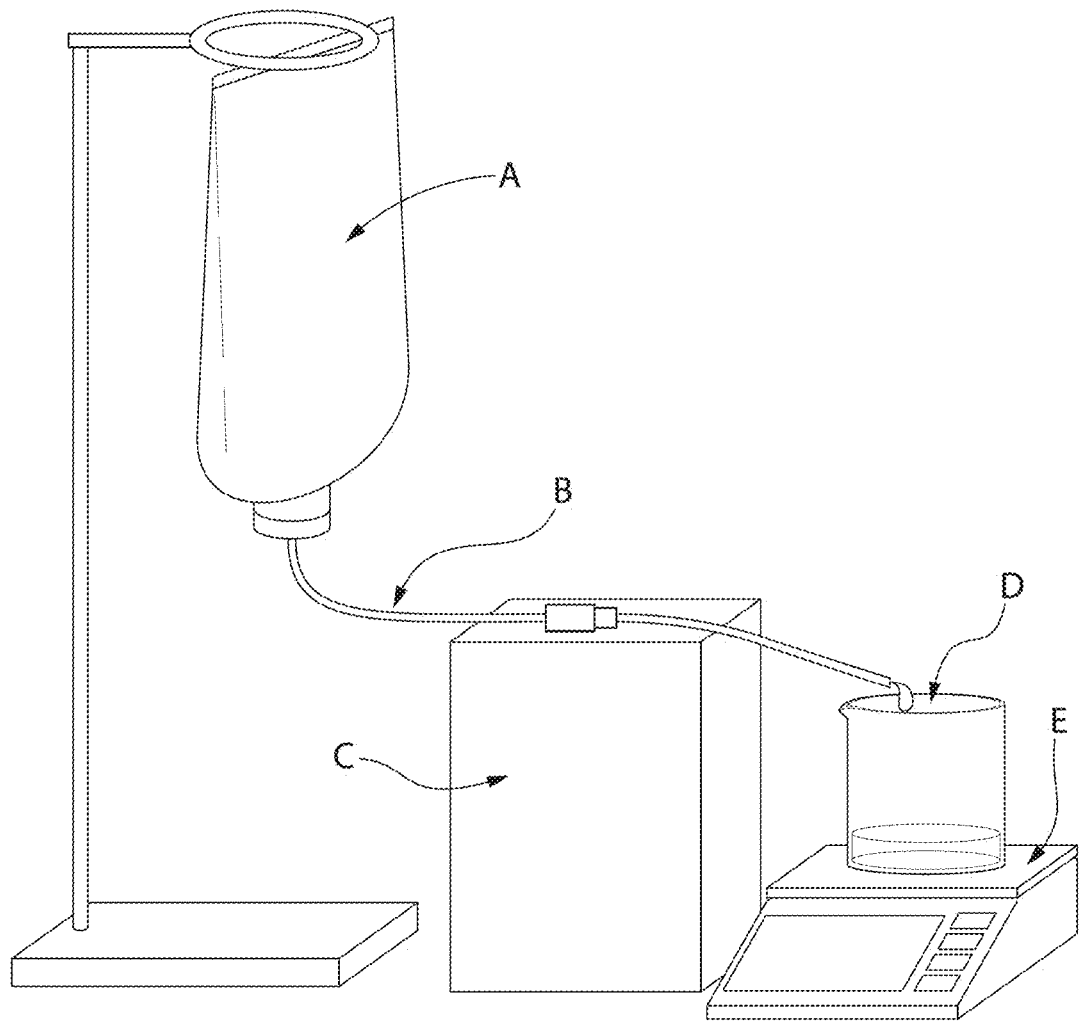
FIG. 36 depicts a drainage model experiment setup using the device of the present invention.

In vitro experiments simulated drainage of serous/purulent fluid (FIG. 36). In this experimental setup a 14 French drainage catheter (Total Abscession; Angiodynaics; Queensbury, N.Y.) was inserted into a compressible reservoir. The distal female end of the drainage catheter was then connected to either a Luer connector or Lamprey lock. The reservoir was filled to an initial volume of 500 mL and was elevated above the catheter outlet to a constant fluid column height of 20 cm. Gravity drainage occurred into an open beaker atop an electronic balance (Precision Balances Model ML802T/00; Mettler-Toledo, Greifensee, Switzerland). Mass and time were simultaneously recorded at fixed intervals for a specified duration to determine mean drainage rate, total drainage time, and cumulative drainage or percentage of total volume drained. To calculate drainage rate, units of mass were converted to volume by dividing mass by specific gravity. Each experimental condition was repeated 5 times and results were averaged across trials and the mean performance of Luer and Lamprey lock connectors were compared.

Figure 37:
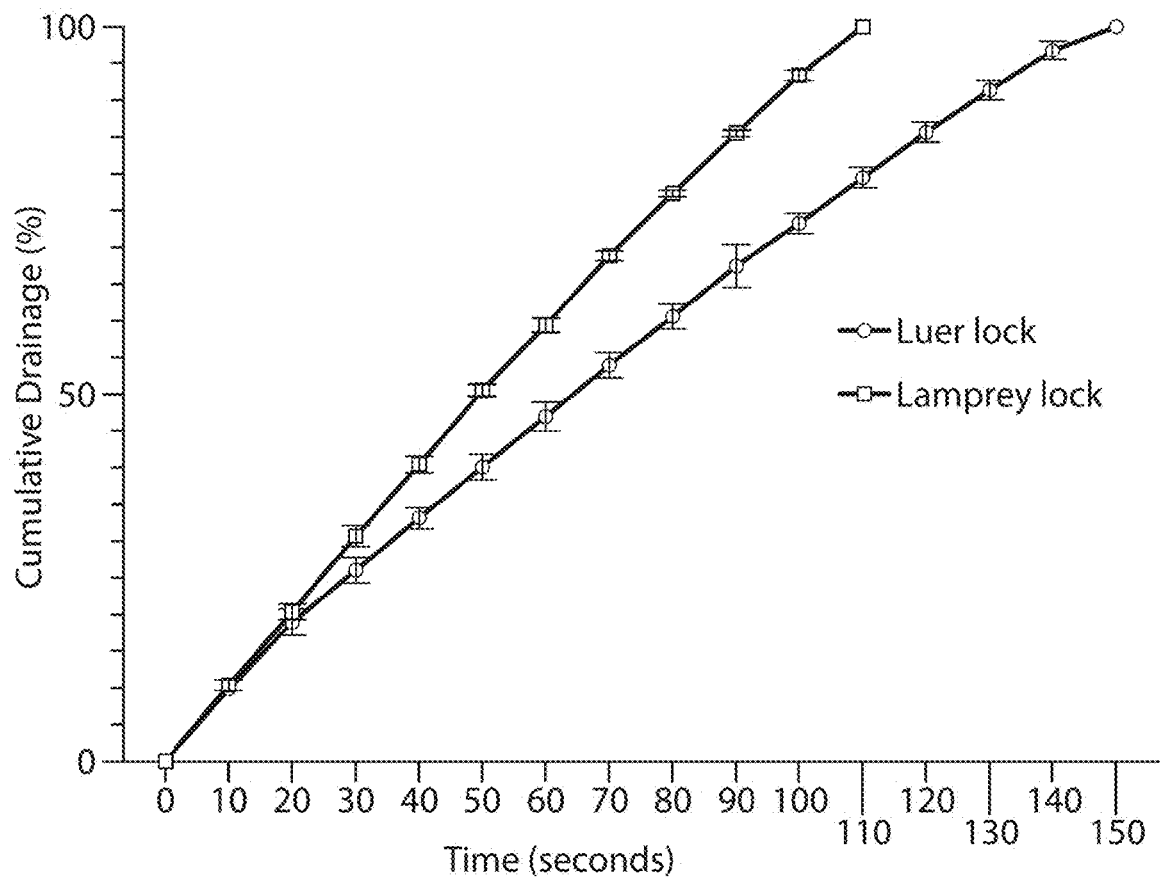
FIG. 37 depicts a serous model.
Figure 38:
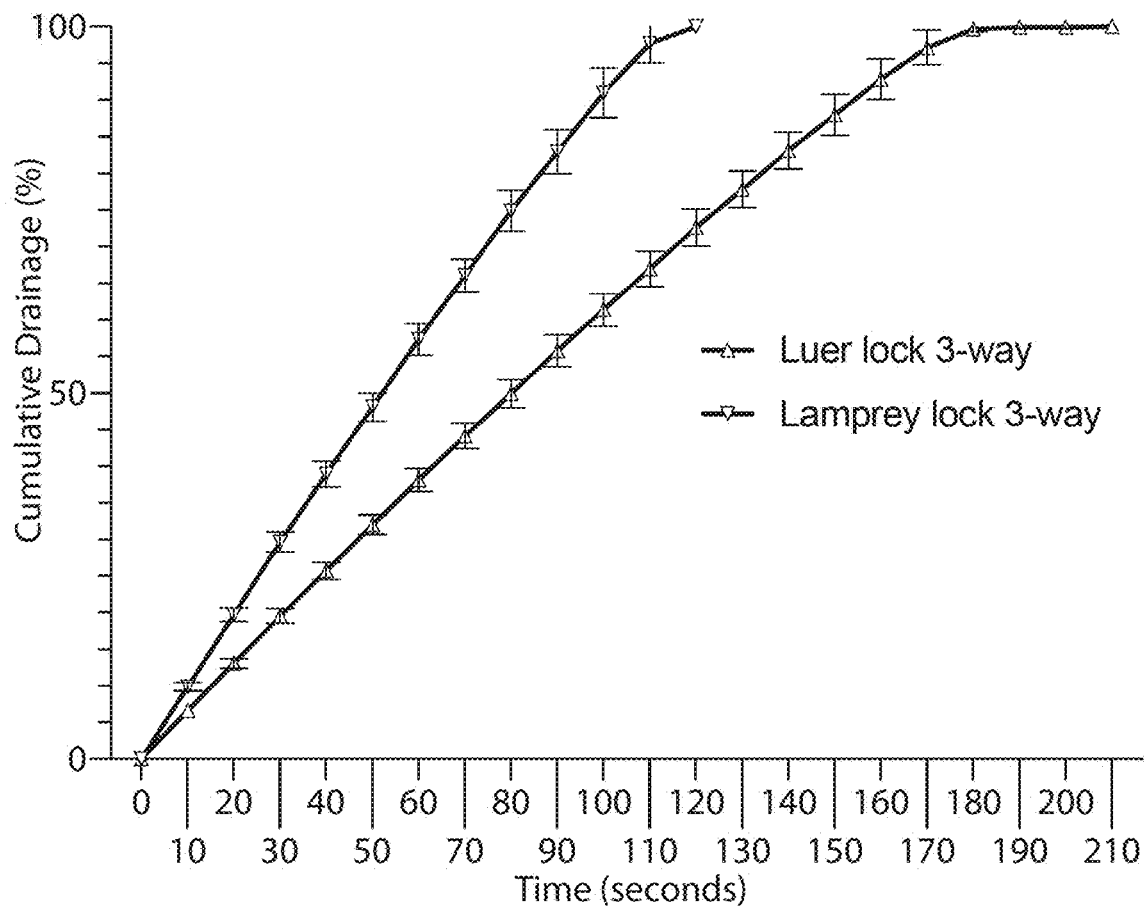
FIG. 38 depicts a serous 3-way model
Figure 39:
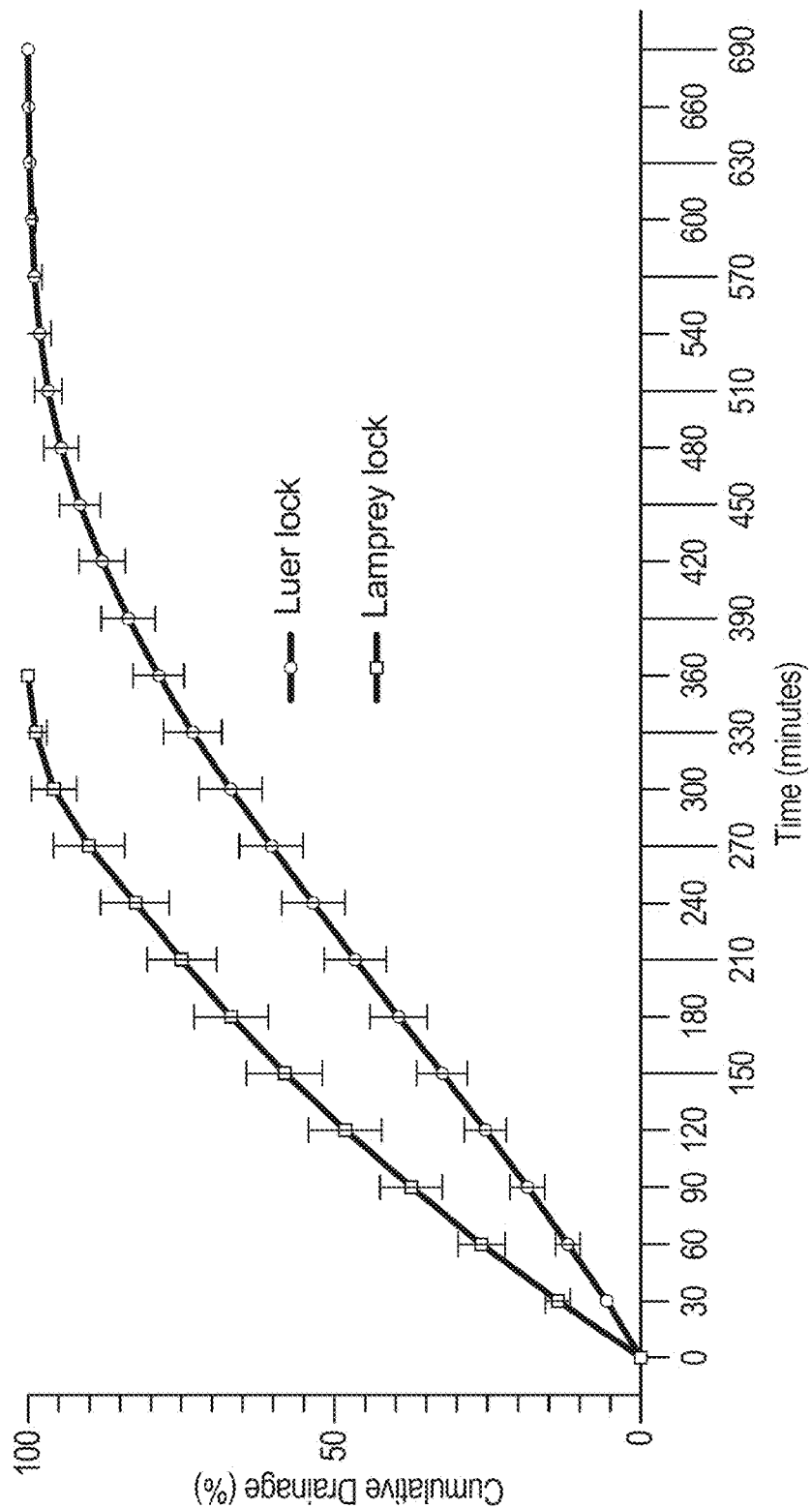
FIG. 39 depicts an abscess model.
Figure 40:
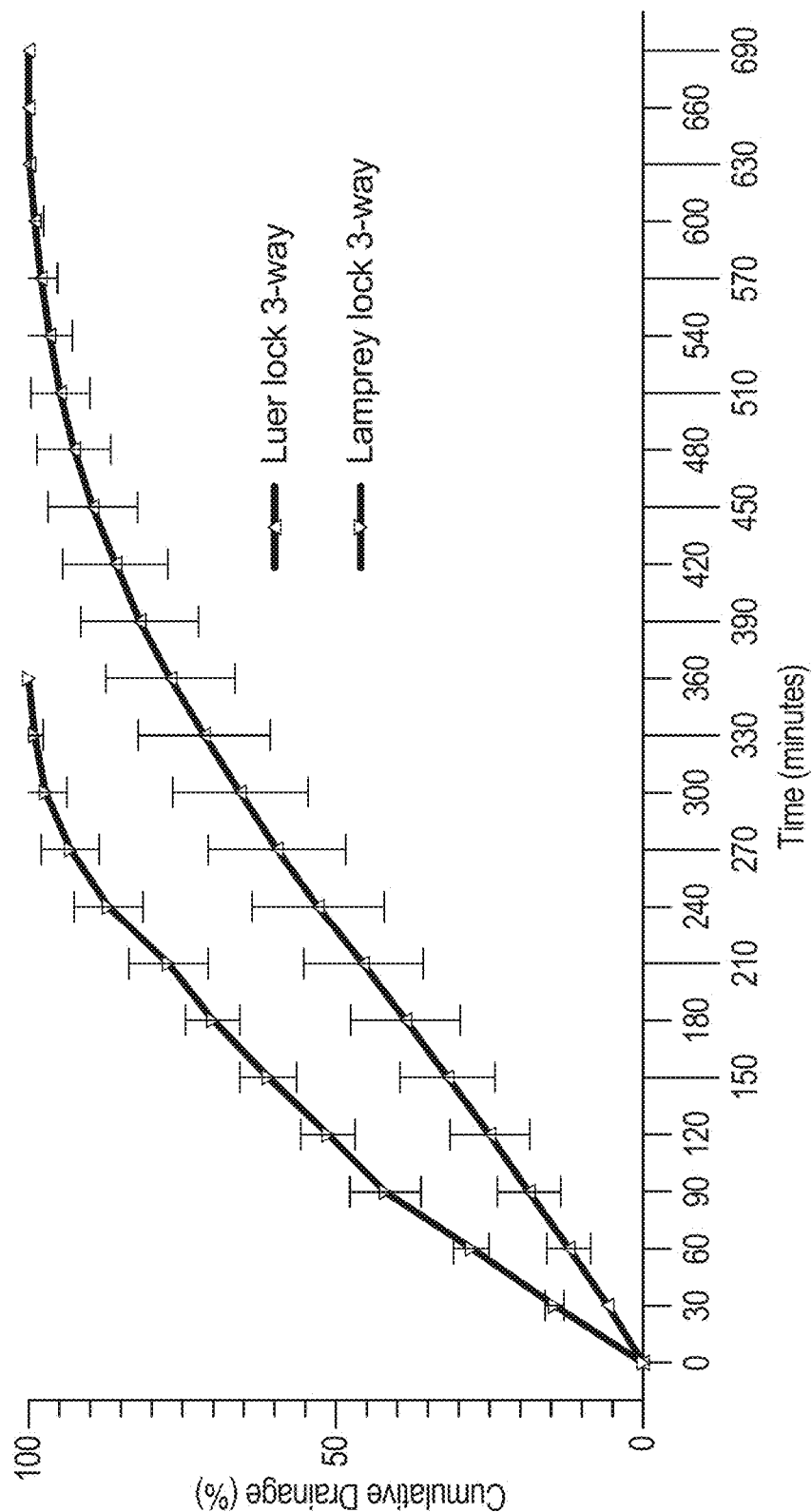
FIG. 40 depicts an abscess 3-way model

In the serous model, the Lamprey lock demonstrated a drainage rate 32.7% faster than the Luer lock (FIG. 37) and the 3-way Lamprey lock drainage rate was 56.7% faster than the 3-way Luer lock (FIG. 38). In the abscess model, the Lamprey lock has a drainage rate 92.3% faster than the Luer lock (FIG. 39) and the 3-way Lamprey lock drainage rate is 104.5% faster than the 3-way Luer lock (FIG. 40).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A lamprey lock device comprising:
   a tubular shaped housing having a proximal end, a distal end and length therebetween, the housing further having an external surface and an internal surface, such that a lumen is formed within the internal surface along the housing length;
   an O-ring having an inner diameter and positioned within the lumen at the distal end;
   a first luer taper adapter having an inner diameter and positioned within the lumen and proximal to the O-ring, wherein the first luer taper adapter has a threaded internal surface; and
   an elastomeric ring having an inner diameter and positioned within the lumen and proximal to the first luer taper adapter;
   wherein the inner diameters of the first luer taper adapter and the elastomeric ring are equal to or greater than the inner diameter of the O-ring.

2. The lamprey lock device of claim 1, wherein the O-ring, the first luer taper adapter and the elastomeric ring each has an internal diameter equal to or greater than 4 mm.

3. The lamprey lock device of claim 1, further comprising a second luer taper adapter positioned within the lumen and proximal to the elastomeric ring, wherein the second luer taper adapter has a threaded internal surface.

4. The lamprey lock device of claim 1, wherein the elastomeric ring has a width of greater than 1 mm.

5. The lamprey lock device of claim 1, further comprising an elastomeric coating on the threaded internal surface of the first luer taper adapter.

6. The lamprey lock device of claim 1, wherein the threaded internal surface of the first luer taper adapter has a spiral rotation of at least 0.5.

7. The lamprey lock device of claim 1, wherein the elastomeric ring has an interior diameter ranging between 5-8 mm.

8. The lamprey lock device of claim 1, further comprising a three-way stopcock comprising:
   a tubular body having a first tube section, a second tube section and a third tube section, wherein each of the first, second and third tube sections comprises a lumen and are fluidly connected at a first end to a central connector and terminate in an opening at a second end opposite to the first end; and
   a central component comprising a circumference that is slightly less than a circumference of the central connector, such that central component may be inserted within the central connector with minimal tolerance, and wherein the central component comprises a first open side, a second open side, a third open side, and a closed side;
   wherein the second end of the first tube section is connected to the distal end of the lamprey lock device;
   wherein the second end of the second tube section is fluidly connected to a flush pump; and
   wherein the second end of the third tube section is fluidly connected to a drainage reservoir.

9. The lamprey lock device of claim 8, wherein the stopcock comprises:
   a drain mode, wherein the central component produces a channel from the first open side and the third open side into the drainage reservoir; and a flush mode, wherein the central component produces a channel from a flush reservoir through the first open side and the second open side into a catheter connected to the lamprey lock device.

10. The lamprey lock device of claim 1, further comprising a tubing having a proximal end, a distal end, and a body therebetween connected to the distal end of the housing, wherein the body comprises a first opening at the proximal end of the tubing and a second opening at the distal end of the tubing, a third opening therebetween and a side port, wherein the side port is fluidly connected to the body through the third opening.

11. The lamprey lock device of claim 10, wherein the side port comprises a first end, a second end and a lumen therebetween, wherein the second end comprises an opening, sized and configured to connect to standard sizing for luer connectors.

12. The lamprey lock device of claim 10, wherein the side port further comprises a valve member configured to allow selective fluid communication between the body and the side port, wherein the valve member comprises a compressible component configured to receive a luer tip of a syringe at the second end, a support structure configured to guide the compressible component through travel along the lumen of the tube from the second end to the first end and at least one channel configured to open when the compressible component receives the luer tip of the syringe.

13. The lamprey lock device of claim 10, further comprising a flow switch positioned on the body and distal to the side port.

14. The lamprey lock device of claim 13, wherein the flow switch comprises a tab, a track configured to allow longitudinal movement of the tab between an open and close positions, a compressible tubing positioned, and an occluding member configured to move vertically pushing on the compressible tubing causing flow restriction between the body and a drainage reservoir.

15. The lamprey lock device of claim 10, wherein the device further comprises an external clamp positioned distal to the side port and around the body.

16. The lamprey lock device of claim 15, wherein the external clamp comprises a rounded opening and an occluded slot, wherein the rounded opening converges to create a narrow width of the occluded slot, and wherein when body is forced into the occluding slot, the side wall of the body is pinched together and prevents the flow of fluid therethrough.

17. The lamprey lock device of claim 10, further comprising a chamber positioned anywhere between the first opening and the second opening and is configured to engage the exterior surface of the body.

18. The lamprey lock device of claim 17, wherein the chamber further comprises a first end, a second end, and a side port positioned at the first end and a bottom part positioned at the second end, and wherein the side port is fluidly connected to the body through a side channel.

19. The lamprey lock device of claim 18, wherein the side port comprises a valve member configured to allow selective fluid communication between the body and the side port, wherein the valve member comprises a compressible component configured to receive a luer tip of a syringe and a tip positioned below the compressible component, wherein once the syringe is inserted, the luer tip pushes the compressible component down on the body all the way to the bottom part, which in turn causes the side channel to open and allow fluid communication between the side port and the body.

* * * * *